United States Patent
Bayer et al.

(10) Patent No.: US 10,632,262 B2
(45) Date of Patent: Apr. 28, 2020

(54) DRIVE MECHANISM FOR A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Michael Pfoser, Kohlscheid (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 676 days.

(21) Appl. No.: 14/782,664

(22) PCT Filed: Apr. 8, 2014

(86) PCT No.: PCT/EP2014/056971
§ 371 (c)(1),
(2) Date: Oct. 6, 2015

(87) PCT Pub. No.: WO2014/166893
PCT Pub. Date: Oct. 16, 2014

(65) Prior Publication Data
US 2016/0045665 A1    Feb. 18, 2016

(30) Foreign Application Priority Data
Apr. 10, 2013   (EP) ..................................... 13163071

(51) Int. Cl.
*A61M 5/20* (2006.01)
*A61M 5/315* (2006.01)

(52) U.S. Cl.
CPC .............. *A61M 5/315* (2013.01); *A61M 5/20* (2013.01); *A61M 5/3157* (2013.01);
(Continued)

(58) Field of Classification Search
CPC .............. A61M 5/315; A61M 5/31563; A61M 5/51311; A61M 2005/3154; A61M 5/31541; A61M 5/31548; A61M 5/3155
See application file for complete search history.

(56) References Cited

U.S. PATENT DOCUMENTS 5,226,895 A * 7/1993 Harris ................... A61J 1/1406
  604/208
2008/0287883 A1* 11/2008 Radmer .............. A61M 5/3155
  604/211

(Continued)

FOREIGN PATENT DOCUMENTS

CN      101115520    1/2008
CN      101262899    9/2008

(Continued)

OTHER PUBLICATIONS

International Preliminary Report on Patentability in International Application No. PCT/EP2014/056971, dated Oct. 13, 2015, 7 pages.

(Continued)

*Primary Examiner* — Nathan R Price
*Assistant Examiner* — Courtney B Fredrickson
(74) *Attorney, Agent, or Firm* — Fish & Richardson P.C.

(57) ABSTRACT

This disclosure relates to a drive mechanism for a drug delivery device and to a respective drug delivery device. The drive mechanism includes an elongated housing extending in an axial direction, an actuation member rotatably supported on the housing for setting of the dose. The drive mechanism further includes a last dose sleeve directly rotatably engaged with the actuation member and having at least one stop and a last dose member threadedly engaged with the last dose sleeve. The last dose member is further rotatably fixed to the housing and is operable to engage with the at least one stop to limit a rotation of the last dose sleeve.

20 Claims, 16 Drawing Sheets

(52) U.S. Cl.
CPC .... *A61M 5/31511* (2013.01); *A61M 5/31541* (2013.01); *A61M 5/31543* (2013.01); *A61M 5/31553* (2013.01); *A61M 5/31583* (2013.01); *A61M 2005/3154* (2013.01); *A61M 2205/581* (2013.01); *A61M 2205/582* (2013.01)

(56) References Cited

U.S. PATENT DOCUMENTS

| | | |
|---|---|---|
| 2008/0306445 A1 | 12/2008 | Burren et al. |
| 2009/0137964 A1 | 5/2009 | Enggaard et al. |
| 2009/0299297 A1* | 12/2009 | Moller ............... A61M 5/24 604/211 |
| 2010/0324494 A1* | 12/2010 | Plumptre ......... A61M 5/31551 604/207 |
| 2011/0054412 A1 | 3/2011 | Eich et al. |

FOREIGN PATENT DOCUMENTS

| | | |
|---|---|---|
| WO | WO 2004/078239 | 9/2004 |
| WO | WO 2006/084876 | 8/2006 |
| WO | WO 2007/030957 | 3/2007 |
| WO | WO 2009/132778 | 11/2009 |
| WO | WO 2010/139645 | 12/2010 |
| WO | WO 2012/062912 | 5/2012 |

OTHER PUBLICATIONS

International Search Report and Written Opinion in International Application No. PCT/EP2014/056971, dated Jun. 3, 2014, 12 pages.

* cited by examiner

A-A

B-B

C-C

D-D

E-E

F-F

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/056971, filed on Apr. 8, 2014, which claims priority to European Patent Application No. 13163071.7, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector comprising a last-dose limiting, hence, an end-of-content mechanism.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing, adapted to receive a cartridge at least partially filled with the medicament to be dispensed. The device further comprises a drive mechanism, typically having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge can be replaced by a new one. In contrast to that, drug delivery devices of disposable type are to be entirely discarded when the medicament in the cartridge has been dispensed or used-up.

With such multi-dose drug delivery devices at least a last dose limiting mechanism is required to inhibit setting of a dose exceeding the amount of medicament which is left in the cartridge. This is to avoid a potentially dangerous situation for the user believing that a set dose is entirely injected.

There already exist some drug delivery devices with such end-of-content mechanisms or last dose mechanisms.

Document WO 2009/132778 A1 for instance discloses a dose limiting member designed for axial movement in a proximal direction with respect to the piston rod during dose setting. The dose limiting member comprises a first stop element and the piston rod comprises a second stop element. First and second stop elements stop an axial movement of the dose limiting member in the proximal direction with respect to the piston rod when the first and second stop elements catch, thereby limiting a movement of the dose setting member for increasing a set dose of medication to be delivered. There, the dose limiting member and the piston rod only interact directly, when the first and second stop elements catch.

End-of-content mechanisms or last dose limiting mechanisms of drug delivery devices of e.g. pen-injector type are typically located and implemented to directly or indirectly engage with the piston rod of the drive mechanism. Since the axial position of the piston rod is unequivocally related to the axial position of the piston in the cartridge it provides a direct indication of the amount of medicament remaining in the cartridge.

Additionally or alternatively, last dose limiting mechanisms may also be implemented by the mechanical interaction of a drive sleeve being either directly or indirectly coupled and engaged with the piston rod, at least during a dose dispensing procedure.

With most of these known approaches the last dose limiting mechanism is located rather remote from an actuation member, such like a dose dial member, by way of which the user may interact with the drive mechanism, e.g. for setting and/or dispensing of a dose. For limiting or delimiting a dose setting procedure, the angular momentum or driving force exerted by a user of the device has to be transferred from the actuation member almost through the entire drive mechanism and the plurality of its mutually interacting components until the last dose limiting mechanism is eventually activated and blocks a further dose incrementing movement of the drive mechanism and of its various components.

Since the mechanically interacting components of a drive mechanism are always subject to inevitable mechanical tolerances, a respective tolerance chain extending between the actuation member and the last dose limiting mechanism is fairly long. In effect, once a last dose limiting mechanism is activated and actually inhibits a dose incrementing displacement of e.g. a drive sleeve relative to a housing or relative to a piston rod, the locking or blocking of e.g. the drive sleeve has to propagate and to be transferred or returned to the actuation member. Also here, due to the tolerance chain at least a minimal displacement, e.g. rotation of the actuation member, may still be possible even though a dose incrementing displacement of the drive mechanism is effectively blocked.

It is therefore an object of the present invention to avoid disadvantages of known drug delivery devices and to provide an improved last dose limiting mechanism.

It is another object of the present invention to provide a drive mechanism for a drug delivery device for setting and dispensing of a dose of a medicament typically provided in a cartridge, wherein the drive mechanism is equipped with a last dose limiting mechanism. It is a further object to provide an alternative end-of-content mechanism or an alternative last dose limiting mechanism operable to provide an accurate and immediate feedback to the user of the device in a last dose limiting configuration. Moreover, the last dose limiting mechanism should be highly reliable and robust.

In a further aspect the invention aims to provide a drug delivery device comprising such a drive mechanism and comprising a cartridge sealed with a piston to become operably engaged with a piston rod of such drive mechanism.

The present invention provides a drive mechanism for a drug delivery device for dispensing of a dose of a medicament. The drive mechanism comprises an elongated housing extending in an axial direction. The elongated housing is typically of tubular or cylindrical shape and serves to accommodate mechanically interacting components of the drive mechanism that are required to displace a piston rod in a distal direction to engage with a piston of a cartridge being at least partially filled with a medicament to be dispensed by the drug delivery device.

The drive mechanism is typically operable to set and to dispense multiple doses of the medicament of variable size. Hence, the drive mechanism is operable in a dose setting mode for selecting or individually setting of a dose of the medicament. After setting of a dose, the set dose can be dispensed by the drive mechanism when switched into a dose dispensing mode. Operation of the drive mechanism in at least the dose setting mode can be controlled and driven by an actuation member rotatably supported on the housing for setting of the dose.

Optionally, the actuation member may also serve to operate the drive mechanism for dispensing of the previously set dose. Typically, the actuation member is located at a proximal end of the housing located opposite and facing away from a dispensing end of the drug delivery device.

The drive mechanism further comprises a last dose sleeve rotatably engageable with the actuation member at least during a dose setting procedure and having at least one stop to limit a displacement of a last dose member threadedly engaged with the last dose sleeve and being rotatably fixed to the housing. The last dose member also belongs to the drive mechanism and is adapted to lock, to block or to impede a dose incrementing displacement, i.e. a dose incrementing rotation of the last dose sleeve when a last dose limiting configuration of the drive mechanism has been reached. Preferably, the last dose sleeve is directly engaged with the actuation member. It may even be at least partially or entirely housed therein. Furthermore, the last dose sleeve may also be permanently rotatably engaged with the actuation member, even when the drive mechanism is in dose dispensing mode.

Preferably, the actuation member is rotatably supported on the housing and can be rotated in two opposite directions, in particular for incrementing and for decrementing a dose during a dose setting procedure. At least in the dose setting mode, the actuation member and the last dose sleeve are rotatably coupled and rotatably locked with respect to each other, so that a rotation of the actuation member relative to the housing is unalteredly transferred and coupled to or with a respective rotation of the last dose sleeve relative to the housing.

Since the last dose member is threadedly engaged with the last dose sleeve and since the last dose member is rotatably fixed to the housing, e.g. splined to the housing, the last dose member is forced to travel in axial direction relative to the housing and/or relative to the last dose sleeve during a dose setting procedure. Since the last dose member is rotatably fixed to the housing it cannot rotate neither with respect to the housing nor with respect to the last dose sleeve.

When the drive mechanism approaches or reaches a last dose limiting configuration, the last dose member abuts with or engages with the at least one stop, e.g. a last dose stop, thereby limiting and blocking a further dose incrementing rotation of the last dose sleeve. Since the last dose sleeve is directly engaged and mechanically coupled with the actuation member, the actuation member is correspondingly blocked and rotatably locked in the last dose limiting configuration. Moreover, since the actuation member is directly engaged with the last dose sleeve and since a rotation of the last dose sleeve relative to the housing can be blocked by a single last dose member which is directly engaged with the last dose sleeve and with the housing, a rather direct and robust feedback can be provided to a user of the device when the drive mechanism reaches the last dose limiting configuration.

By having the last dose sleeve in direct engagement with the actuation member, a tolerance chain of a last dose limiting mechanism is fairly short and the negative influence of inevitable mechanical tolerances and mechanical play between various functional and mutually engaging components of the drive mechanism can be reduced to a minimum.

Naturally, the travel path the last dose member is allowed to travel along the last dose sleeve is adapted and correlated to the maximum distance the piston rod of the drive mechanism may advance in distal direction during consecutive dose dispensing procedures. Accordingly, the threaded engagement of the last dose sleeve and the last dose member as well as the axial elongation of the last dose sleeve is designed and chosen accordingly in order to match with the size of the cartridge and the amount of medicament contained therein. Moreover, the axial position of the last dose member relative to the dose sleeve is unequivocally correlated and always corresponds to the axial position of the piston rod and hence to the axial position of the piston of the cartridge operably engaged with the piston rod of the drive mechanism.

According to a further embodiment, the last dose sleeve comprises an external thread mating with an internal thread of the last dose member. The internal thread of the last dose member at least partially surrounds the circumference of the threaded portion of the last dose sleeve. Hence, the last dose member, e.g. designed as a last dose nut, is arranged outside the last dose sleeve, on its outer circumference. Preferably, the last dose member surrounds the outer circumference of the last dose sleeve only partially in order to support an easy and intuitive assembly of last dose sleeve, last dose member and housing. By only partially surrounding the circumference of the last dose sleeve, the last dose member can be assembled on the last dose sleeve in radial direction between two axially separated stops of the last dose sleeve.

According to a further embodiment, the at least one stop extends radially outwardly at a distal and/or proximal end of the external thread of the last dose sleeve. Preferably, the external thread terminates at a distal as well as at a proximal end with one stop, respectively. The stop or stop element typically extends radially outwardly from a threaded portion of the last dose sleeve in order to provide a radial stop or radially extending stop face for the last dose member. Typically, the last dose member comprises a leading and a trailing edge in circumferential direction with respect to the sense of rotation of the last dose sleeve relative to the last dose member. By means of its leading and/or trailing edge, the last dose member may engage with the radially extending or radially protruding stop provided on the outer circumference of the last dose sleeve when reaching a last dose limiting configuration.

Generally, radially extending stops provide an accurate, well-defined and reproducable stop configuration for those components being equipped with such mutually engaging stop features. A radial stop generally provides a radially outwardly and/or radially inwardly extending structure provided at a particular tangential position on the inner and/or outer circumference of e.g. a tubular shaped component. In this way, a definite and well defined stop configuration can be provided which is much more precise and less sensitive to an eventual self-locking which may otherwise occur with an axial stop, such like a radially extending flange extending at a particular axial position of e.g. a last dose sleeve.

However, in alternative embodiments implementation of such axial stops is also generally conceivable, also in combination with radially acting stops.

When the leading or trailing edge of the last dose member abuts or engages with the at least one stop of the last dose sleeve, further rotation of the last dose sleeve can be effectively blocked and inhibited, thereby blocking or inhibiting a further dose incrementing rotation of the actuation member during a dose setting procedure. The radially and preferably also axially extending leading or trailing edge of the last dose member and the correspondingly shaped stop of the last dose sleeve are adapted to immediately block a further rotation of the last dose sleeve and hence of the actuation member when a predetermined rotational position of the last dose sleeve and the actuation member has been reached.

According to another embodiment, the last dose member comprises a radially outwardly extending protrusion engaged with an axially extending groove of the housing. In particular, the last dose member is radially sandwiched between the housing and the last dose sleeve. By means of the radially outwardly extending protrusion, the last dose member is splined to the housing and is hence rotatably fixed to the housing. In this context a splined engagement of at least two components means, that the two components are rotatably engaged but are free to move in an axial direction with respect to each other.

Mutually engaging protrusion and groove of the last dose member and the housing only support and allow for an axial displacement of the last dose member relative to the housing and relative to the last dose sleeve. Preferably, the radially outwardly extending protrusion of the last dose member is located midway between opposite circumferential ends, hence midway between trailing and leading edges of the last dose member. Such an arrangement of the protrusion is beneficial in terms of distribution of mechanical forces and momentum acting on the last dose member.

According to another embodiment the last dose member is arc-shaped and comprises a leading and a trailing edge in circumferential direction to engage with the at least one stop. In particular, the arc-shaped geometry of the last dose member corresponds with the outer circumference of the tubular-shaped threaded portion of the last dose sleeve. Preferably, the arc-shaped last dose member extends at most about 180° around the circumference of the last dose sleeve in order to allow for a radially directed mutual assembly of the last dose sleeve and the last dose member.

By having an arc-shaped last dose member extending at least about 90° along the outer circumference of the last dose sleeve, a rather robust, smooth running and reliable mechanical interaction between the last dose member and the last dose sleeve can be effectively provided.

According to a further embodiment, the last dose sleeve and the last dose member are located in a receptacle at a proximal end of the housing. The receptacle may be cup-shaped and allows for an axially and distally directed assembly of the last dose sleeve and the last dose member into the housing of the drive mechanism. Here, it is of particular benefit, when the arc-shaped last dose member is assembled in radial direction on the outer circumference of the last dose sleeve and when in a subsequent step of assembly the combined last dose member and last dose sleeve are corporately assembled and inserted in the proximal receptacle of the housing.

The receptacle of the housing is open in proximal direction to allow for a distally directed assembly of the dose sleeve and the last dose member into the receptacle. In proximal direction, the receptacle can be confined by a radially inwardly extending socket of the housing providing an axial stop and a radially inwardly extending stop face for the last dose sleeve. The receptacle may also receive a distally extending clutch to operably engage with the last dose sleeve and/or with the actuation member.

In a further embodiment, the actuation member is rotatably supported on the proximal end of the housing at least in a dose setting mode of the drive mechanism. The actuation member may be snapped on the proximal end of the housing and may therefore positively engage with the housing at least in axial direction. Hence, a distal end portion of the actuation member may comprise a radially inwardly extending snap feature or a correspondingly shaped flange portion to engage with a radially outwardly extending rim of the housing.

Moreover and according to a further embodiment the actuation member is cup-shaped and surrounds and closes the receptacle of the housing in proximal direction when assembled thereon. Here, the actuation member fulfils a double or even a triple function. First of all, the actuation member serves to transfer an angular momentum to the last dose sleeve and/or to further functional components of the drive mechanism operably engaged therewith. Second, the actuation member may control and trigger a dose dispensing procedure. Third, the actuation member actually seals and closes a proximal end of the housing of the drive mechanism and/or of the drug delivery device.

According to a further embodiment, the actuation member is axially displaceable relative to the housing from a proximal dose setting position to a distal dose dispensing position against the force of at least one spring element. By means of an at least small axial displacement of the actuation member, the drive mechanism is operable to switch between a dose setting mode and a dose dispensing mode. Preferably, axial displacement of the actuation member has no influence on the axial position of the last dose sleeve. Hence, the rotational engagement of the actuation member and the last dose sleeve allows for a mutual axial displacement of the actuation member relative to the last dose sleeve. Preferably, the actuation member is splined to the last dose sleeve for a transfer of angular momentum there between.

According to a further embodiment, the last dose sleeve comprises at least one axially extending recess to receive a correspondingly shaped distally extending journal of the actuation member. Preferably, the axial recess is located at a pre-determined distance from the radial center of the last dose sleeve to allow for a rotational engagement of the actuation member and the last dose sleeve by means of the journal extending into or reaching through the recess of the last dose sleeve. This type of mutual engagement allows for a rotational coupling of the last dose sleeve and the last dose member even at different axial positions of the actuation member relative to the last dose sleeve and/or relative to the housing. Hence, even in a dose dispensing mode, the last dose sleeve and the actuation member remain rotationally coupled and rotationally locked with respect to each other.

Preferably, the last dose sleeve comprises a circumferential rim at its proximal end extending in proximal direction and being interrupted by the at least one axial recess. The inside surface of the rim may flush and may extend into the inside facing portion or side wall of the tubular-shaped last dose sleeve. Hence, the axially extending recess or several recesses of the last dose sleeve are preferably arranged at or near a radially outwardly located circumference of the last dose sleeve in order to keep a mechanical load on the recesses at a minimum level during a rotating dose setting movement of the actuation member.

In a further preferred embodiment, the at least one spring element to engage with the actuation member is located on the last dose sleeve. The spring element is preferably helically shaped, extends in proximal direction from a proximal end of the last dose sleeve and abuts against the inside of a proximal end face of the actuation member. Preferably, there are provided at least two symmetrically arranged spring elements on diametrically opposite portions of the last dose sleeve. In particular, the at least one spring element is integrally formed with the last dose sleeve and may extend from the proximal and circumferentially extending rim located at the proximal end of the dose sleeve.

By means of the at least one spring element located on the last dose sleeve, the actuation member can be biased in proximal direction. Hence, distally directed displacement of the actuation member relative to the housing and/or relative to the last dose sleeve acts against the restoring force provided by the at least one spring element.

Moreover and according to another embodiment, the last dose sleeve comprises a radially extending flange portion at its distal end to axially abut with a radially inwardly extending socket portion of the housing. This way, the last dose sleeve is at least axially fixed in distal direction with regard to the housing. Since the actuation member preferably covers the proximal end of the housing and since the actuation member is axially fixed in proximal direction with respect to the housing, mutual assembly of the housing, of the last dose sleeve and the actuation member, e.g. distally clipped on the housing, comes along with a tensioning of the at least one spring element of the last dose sleeve.

In this way, the at least one spring element not only serves to displace the actuation member in proximal direction during switching of the drive mechanism from a dose dispensing mode into a dose setting mode. Moreover, by way of the at least one spring element the last dose sleeve is also axially secured relative to the housing with respect to the proximal direction.

The radially extending flange portion of the last dose sleeve may also act as a support for the at least one stop extending in radial direction from the external thread of the dose sleeve. Accordingly, the last dose sleeve may also comprise a radially extending flange portion at its proximal end in order to support a correspondingly shaped proximal stop to interact with the last dose member to block and to limit a rotation of the last dose sleeve and the actuation member operably coupled therewith.

Additionally, the two oppositely located radially extending flange portions of the dose sleeve may serve as a guiding structure to support a smooth rotation of the actuation member inside the housing. Hence, the radially outwardly located surface portions of the distal and the proximal flange portions of the last dose sleeve may serve as plain or slide bearings for the rotational movement of the last dose sleeve inside the receptacle of the housing. Hence, the radially outwardly facing side surfaces of the distal and proximal flange portions of the last dose sleeve may glide along an inside facing inner surface of the receptacle of the housing in circumferential direction.

According to another embodiment, the last dose sleeve is also rotatably supported on a sleeve-shaped clutch at least partially extending in axial direction into the interior of the last dose sleeve. Here, the clutch may provide a radially inwardly located bearing for the last dose sleeve. The inside facing sidewall of the last dose sleeve and a correspondingly shaped outside facing portion of the clutch are substantially even shaped and are therefore free of protrusions to allow for a smooth rotation of the last dose sleeve relative to the clutch. In particular, the last dose sleeve is radially sandwiched between the receptacle of the housing and the clutch.

According to a further embodiment, the last dose sleeve comprises a toothed surface at a distal end of its radially inwardly facing sidewall to selectively engage with correspondingly shaped and radially outwardly extending teeth of the clutch. It is of particular benefit, when the last dose sleeve is rotatably coupled and hence rotatably fixed to the clutch during a dose setting procedure and when the last dose sleeve, e.g. by way of a distally directed displacement of the clutch is rotatably releasable from the clutch during a dose dispensing procedure. The clutch in turn may be rotatably coupled with further functional components of the drive mechanism, such like a drive sleeve, which is either directly or indirectly engageable with the piston rod for initiating a distally directed longitudinal displacement of the piston rod during a dose dispensing procedure.

Preferably, a distally directed displacement of the clutch can be achieved by a corresponding distally directed displacement of the actuation member. Hence, the actuation member may abut with a proximal end, e.g. with a proximally located rim of the clutch by means of at least one distally extending journal. Starting from an initial configuration, in which the actuation member rests in a proximal position, which corresponds to the dose setting mode of the drug delivery device, a distally directed displacement of the actuation member is almost unalteredly and directly transferable to a corresponding distally directed displacement of the clutch, thereby disengaging the rotational coupling of the clutch and the last dose sleeve.

With the distally directed dose dispensing displacement of the actuation member, the actuation member may engage with radially inwardly extending teeth or radially inwardly extending protrusions with a toothed ring provided at the outer circumference of the housing, thereby rotatably interlocking the actuation member and the housing. Since the last dose sleeve is rotatably released and decoupled from the clutch and since the actuation member is rotatably fixed and engaged with the housing during a dose dispensing procedure, the clutch may rotate for advancing the piston rod in distal direction while the last dose sleeve remains rather stationary for not further modifying the axial position of the last dose member on the actuation member.

If for instance a dose dispensing procedure is interrupted by prematurely releasing the actuation member, the actuation member will return into its proximal position under the effect of the at least one spring element located on the proximal end of the last dose sleeve. Additionally, the clutch may be accordingly spring biased in axial direction relative to the housing. For this purpose, either the clutch or the housing comprises at least one spring element, which provides a restoring- and proximally directed spring force to axially displace the clutch in proximal direction at the end of a dose dispensing procedure.

Under the effect of this additional spring element, the clutch may automatically return into a rotational engagement configuration with the last dose sleeve. Moreover, since the actuation member may axially abut with the clutch, distally directed displacement of the clutch, e.g. for triggering and initiating a dose dispensing procedure, may occur against the action of two separate spring elements, one of which acting between the last dose member and the actuation member and the other of which acting and being located between the housing and the clutch. Naturally, the housing and the clutch comprise mutually corresponding radially inwardly and/or radially outwardly extending protrusions, between which a respective spring element may extend in axial direction.

In general, the last dose mechanism according to the present invention is functionally located between an actuation member, to be directly operated and manipulated by a user of the device, and force- or momentum transmitting components of the drive mechanism. In terms of a flow of force or flow of momentum provided by the drive mechanism, in particular during a dose setting procedure, the last dose limiting mechanism is located upstream of a clutch, upstream of a drive sleeve, upstream of a drive nut as well as upstream of a piston rod of the drive mechanism.

In particular the last dose limiting mechanism directly engages with the actuation member of the drive mechanism which is to be manually operated by a user of the device. In this way, a comparatively direct and robust as well as reliable feedback can be provided to a user of the device when the last dose limiting configuration of the drive mechanism has been reached.

According to another aspect, the invention also relates to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

The cartridge holder may be non-releasably engaged and connected to the proximal housing, e.g. by means of bonding or welding. For reusable drug delivery devices it is of particular benefit when the cartridge holder is detachable from the housing for providing access to the cartridge located therein, in particular for replacing the cartridge. A detachable connection of cartridge holder and housing can be attained by means of mutually corresponding threaded portions of cartridge holder and housing, respectively. Alternatively, it is also conceivable that cartridge holder and proximal housing of the drug delivery device are integrally formed.

Apart from that, the drug delivery device and the drive mechanism may comprise further functional components, such like an actuation member, by way of which a user may operate or manipulate the drug delivery device and its drive mechanism for setting and correcting as well as for dispensing of a correspondingly set dose.

Moreover, the drive mechanism and the drug delivery device may also comprise a dose indicating sleeve, which may rotate together with the drive sleeve and which may provide a visual indication to the user regarding the size of the dose actually set.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The drive mechanism particularly serves to displace a piston rod in axial direction for the purpose of dispensing of a dose of a medicament. In addition, the drive mechanism typically comprises components which also form part of and have a function in at least one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arc(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a brief description of the drawings is provided, in which.

DETAILED DESCRIPTION

Figure 2:
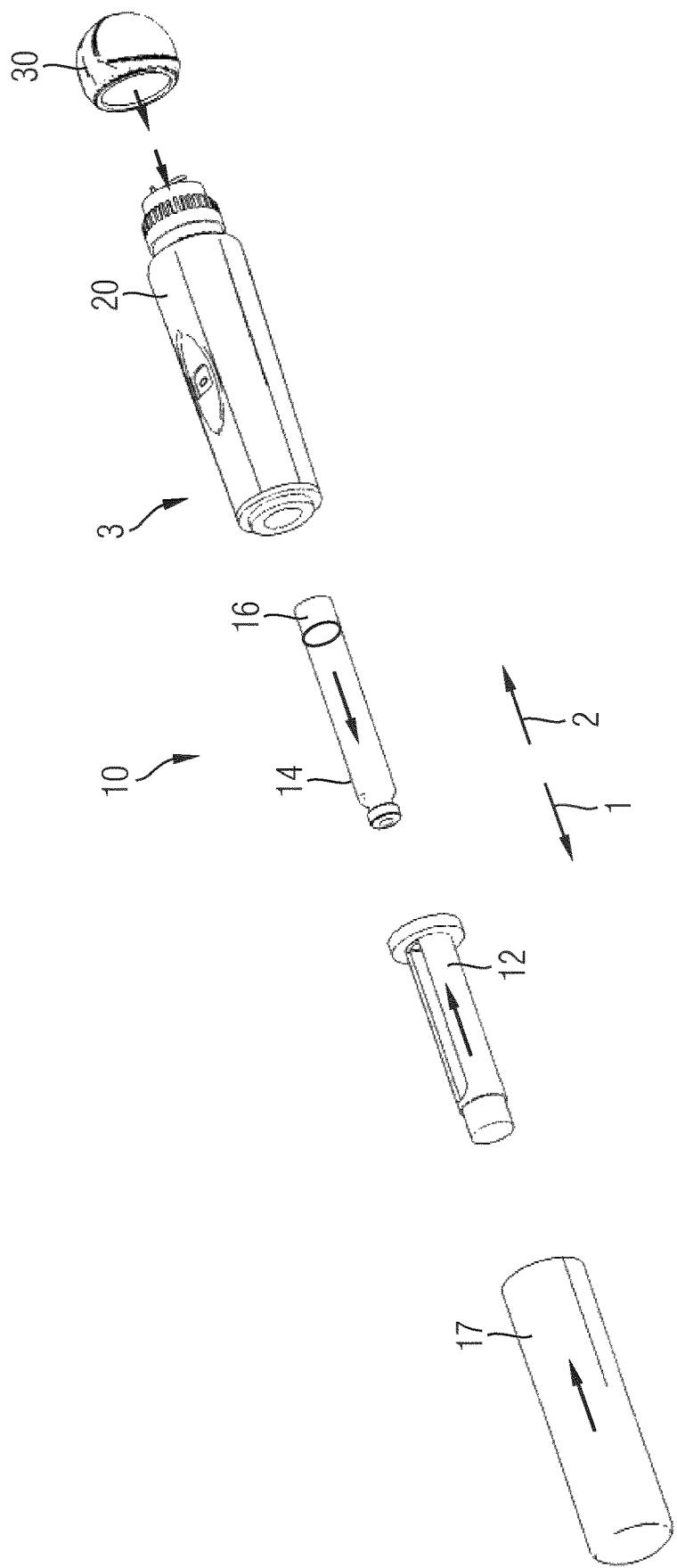
FIG. 2 shows an exploded illustration of the drug delivery device with the drive mechanism assembled in the housing.

In FIG. 2, the drug delivery device 10 is illustrated in an exploded view. The drug delivery device 10 of pen-injector type and comprises a substantially cylindrical and axially elongated shape. Throughout the Figures, the axial distal direction is denoted with reference number 1 and the opposite proximal direction is denoted with reference number 2. The drug delivery device 10 which is also shown in an assembled configuration in FIG. 4 in longitudinal cross section comprises a drive mechanism 3 arranged in a proximal housing 20. In distal direction, the housing 20 is connected with a cartridge holder 12 which is adapted to accommodate and to receive a cartridge 14 containing the medicament to be dispensed by the drug delivery device 10. The cartridge 14 typically comprises a vitreous barrel of cylindrical shape which is sealed in distal direction by a pierceable sealing member, such like a septum.

In proximal direction 2, the cartridge 14 is sealed by a piston 16 slideably arranged in the vitreous barrel of the cartridge 14. Displacement of the piston 16 in distal direction 1 leads to a respective built-up of a fluid pressure inside the cartridge 14. When the distal outlet of a cartridge 14 is connected with e.g. a needle assembly 18, as for instance indicated in FIG. 4, a predefined amount of the liquid medicament contained in the cartridge 14 can be expelled and dispensed via a injection needle of the needle assembly 18, which is not particularly illustrated here.

Figure 4:
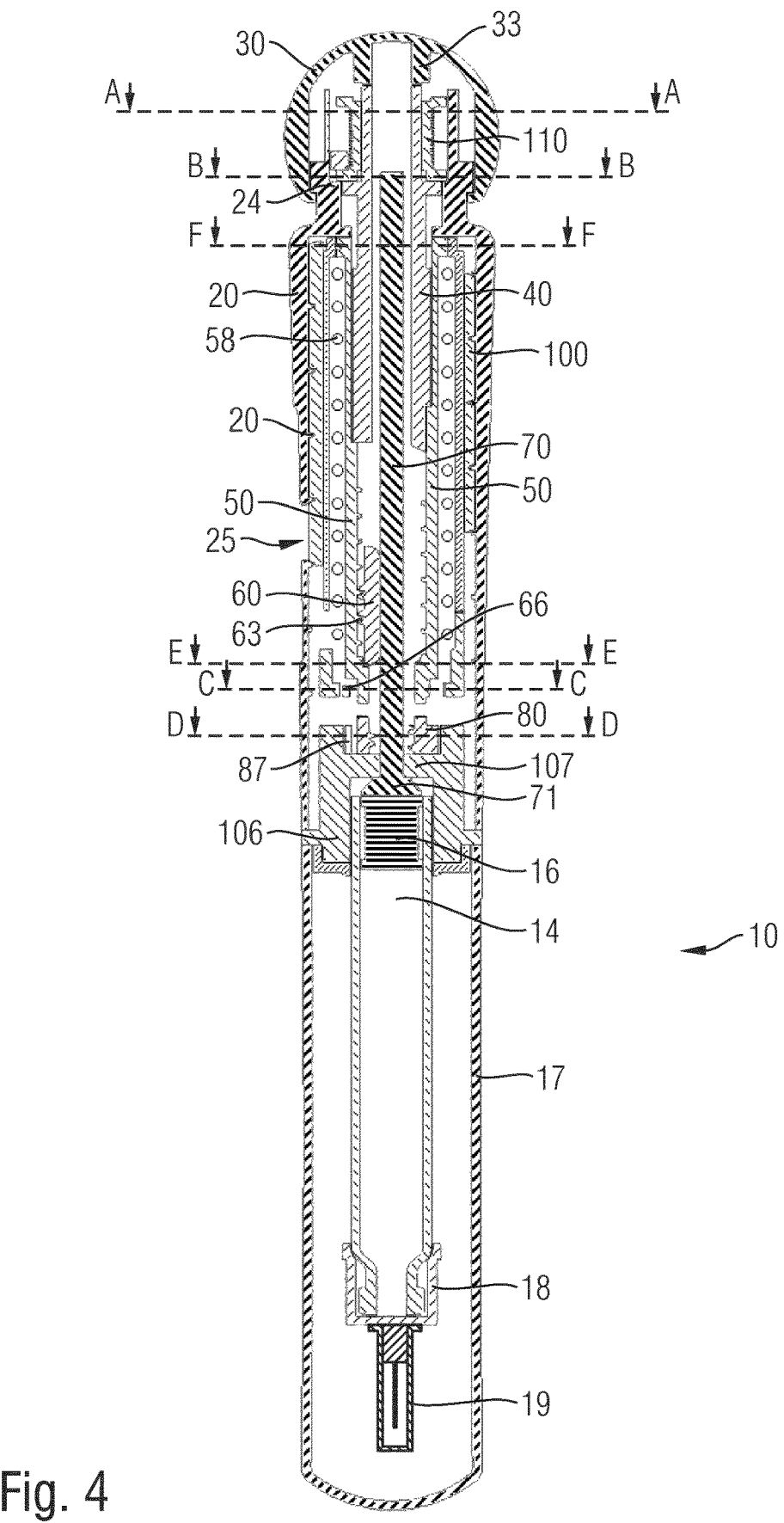
FIG. 4 is illustrative of a longitudinal cross section of the assembled drug delivery device.

In FIG. 4 however, an inner needle cap 19 to protect the double-tipped injection needle is schematically indicated. The needle assembly 18 is typically arranged on a distal end portion of the cartridge holder 14. Typically, a distally located socket of the cartridge holder 12 and the needle assembly 18 comprise mutually corresponding threads to screw the needle assembly 18 onto the cartridge holder 12 in a releasable and removable way.

The cartridge holder 12 is to be protected and covered by a protective cap 17 which is shown in FIGS. 2 and 4. Prior to setting and/or dispensing of a dose, the protective cap 17 as well as the inner needle cap 19 are to be removed. After dispensing or injecting of the medicament into biological tissue, the needle assembly 18 is typically to be discarded and the distal end of the drug delivery is to be covered by the protective cap 17.

The drive mechanism 3 as illustrated in an exploded view in FIG. 3 and as shown in cross section in its fully assembled configuration in FIG. 4 comprises numerous functional components by way of which a dose of variable size can be set and subsequently dispensed.

The dose dispensing procedure comes along with a distally directed advancing displacement of the piston rod 70 relative to the housing 20. The drive mechanism 3 therefore comprises at least a housing 20, a piston rod 70 and a drive sleeve 50 which can be released and operably engaged with the piston rod 70 for selectively setting and dispensing of a dose. Moreover, the drive mechanism 3 comprises a dose limiting member 60 which is engaged with the drive sleeve 50 as well as with the piston rod 70. Mutual engagement of the dose limiting member 60 with both, the drive sleeve 50 and with the piston rod 70 is such, that the dose limiting member is displaced in axial direction, hence in distal and/or proximal direction 1, 2 relative to the drive sleeve 50 when the drive sleeve 50 rotates relative to the piston rod 70 during a dose setting procedure.

Figure 3:
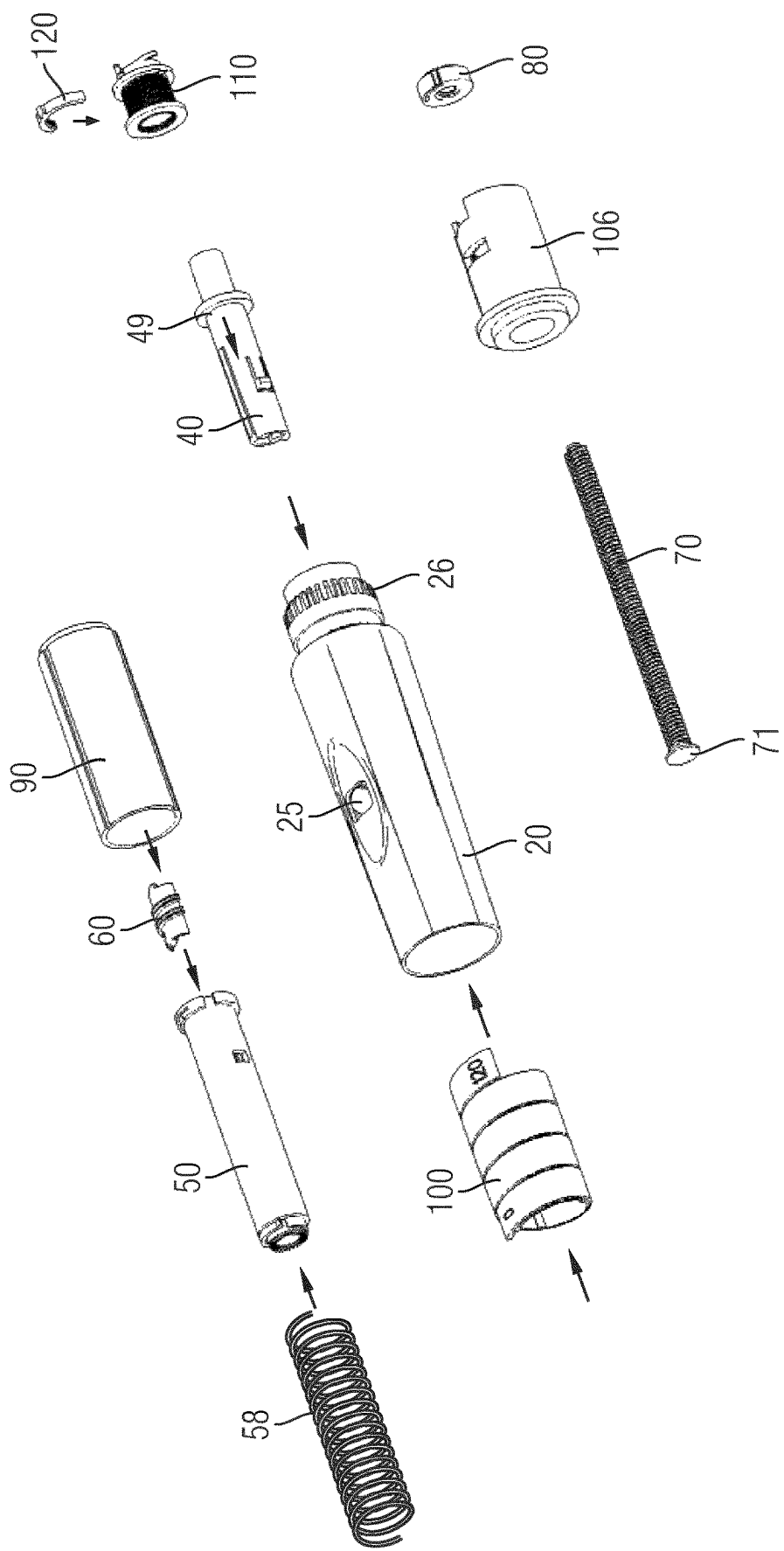
FIG. 3 illustrates various components of the drive mechanism in an exploded view.

Apart from the drive sleeve 50, the dose limiting member 60 and the piston rod 70, the drive mechanism 3 comprises a number of further components as illustrated in FIG. 3. These components together with the actuation member 30 as shown in FIGS. 2 and 4 inter alia serve to visually indicate the size of set dose to a user and further serve to transfer a rotational and/or axial displacement of the user-operated actuation member 30 into respective rotational and/or axial displacement of the drive sleeve 50 for dose setting and/or dose dispensing purpose.

It is to be noted here, the embodiments as illustrated in FIGS. 1 to 20a are only exemplary for one of a plurality of conceivable drive mechanisms that may be equipped with the single dose limiting mechanism as well as the last dose limiting mechanism according to the present invention.

In the following, setting of a dose is described.

Figure 8A:
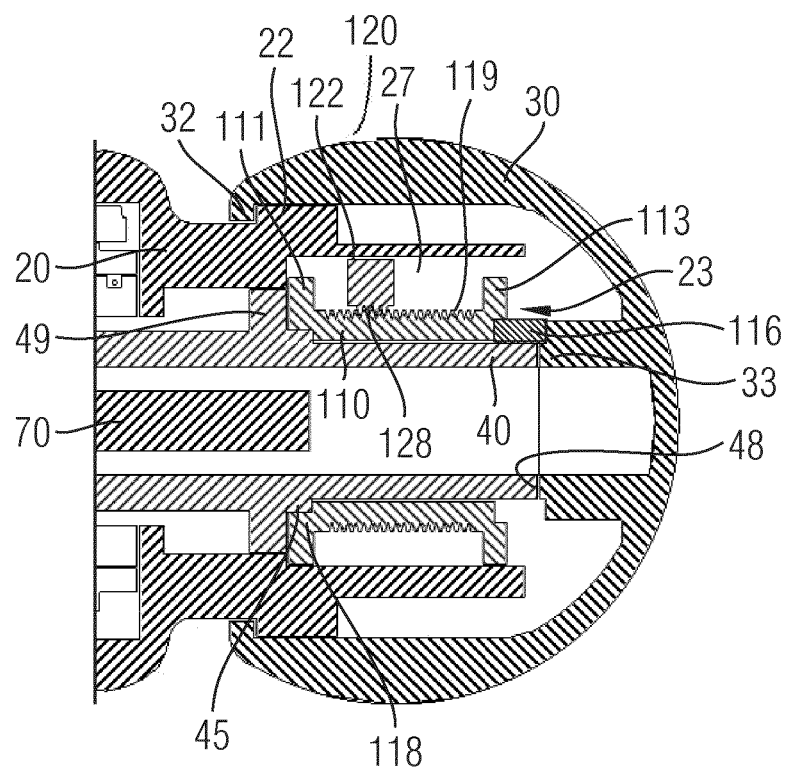
FIG. 8a shows a partial cross section through the proximal end of the drive mechanism during dose setting.
Figure 8B:
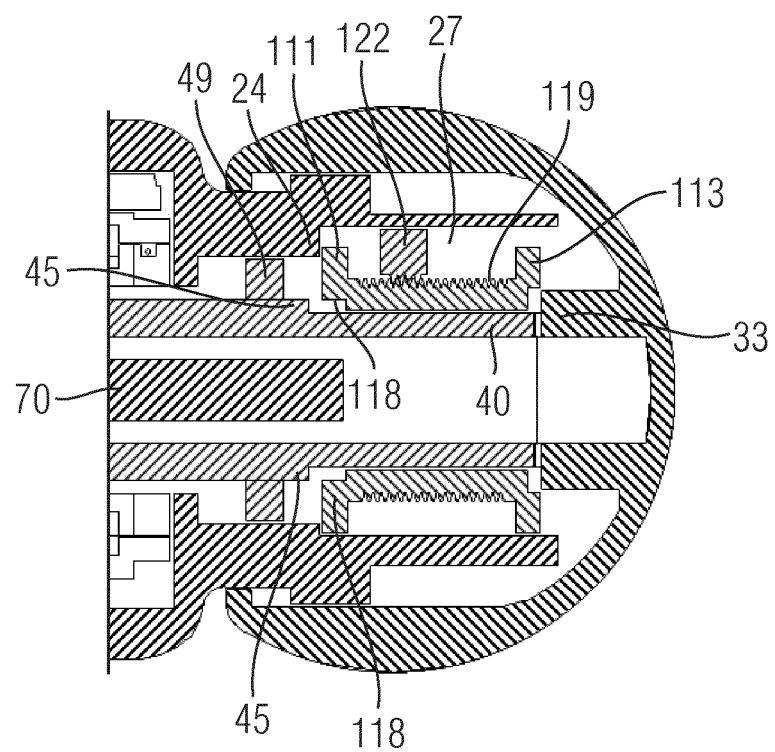
FIG. 8b shows a corresponding cross section during dose dispensing, and FIG. 8c schematically and perspectively illustrates the proximal end of the assembled drive mechanism partially cut, FIG. 9 schematically illustrates the arrangement of the dose limiting member between piston rod and drive sleeve in a perspective and cut view.
Figure 8C:
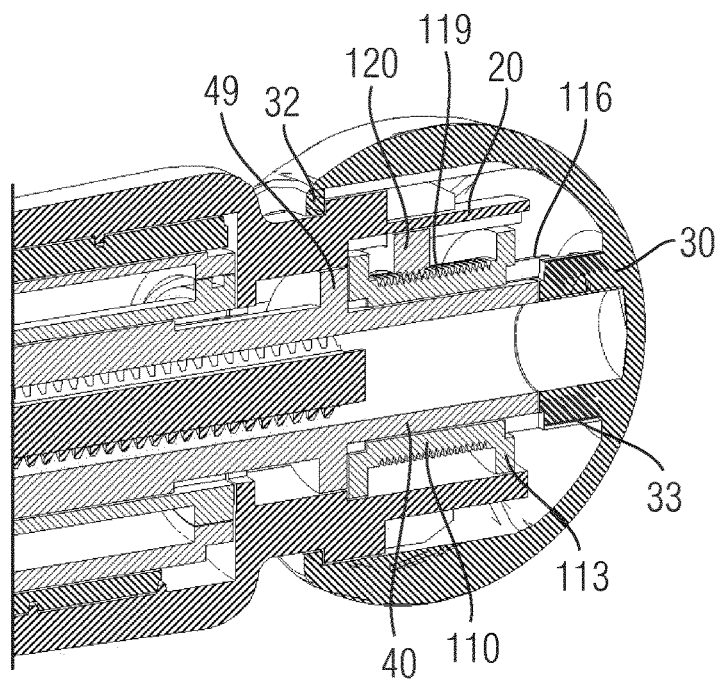
Figure 9:
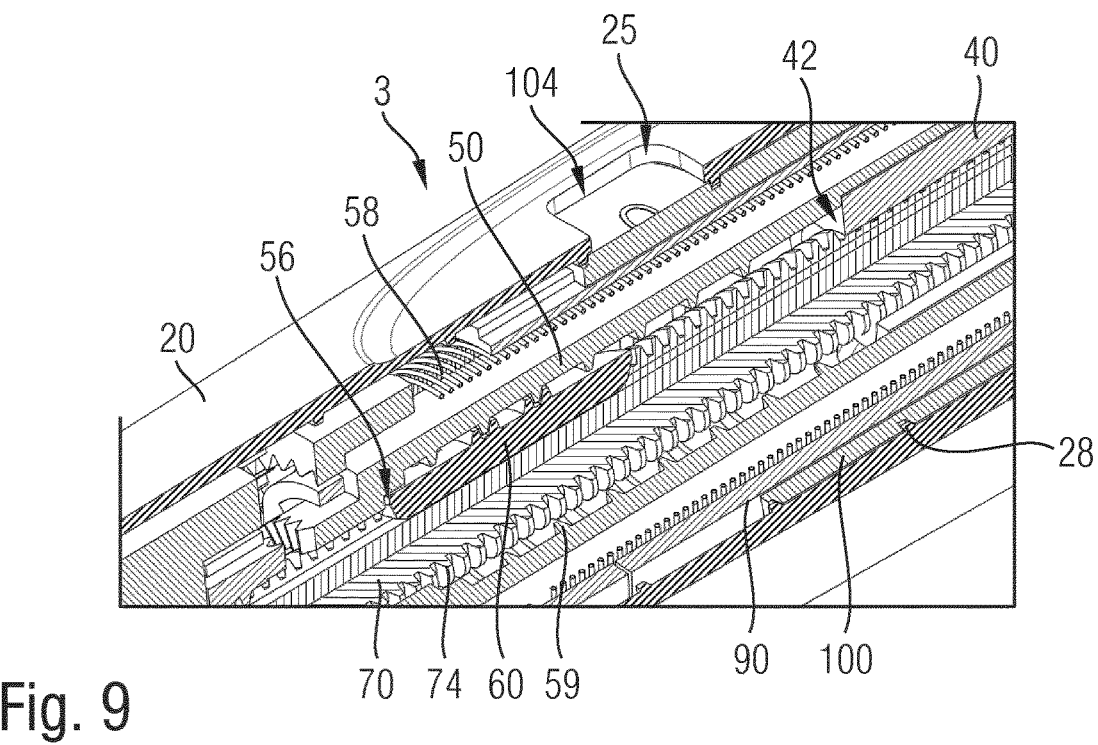

For setting of a dose, the user grips the actuation member 30 located at the proximal end of the housing 20. The actuation member 30 comprises a radially inwardly extending flange portion 32 at its distal end as indicated in FIGS. 8a to 8c, which in a proximally located configuration according to FIG. 8a axially abuts with a radially outwardly extending rim 22 of the housing 20.

The housing 20 further comprises a proximal and tubular shaped receptacle 23 to receive a substantially tubular shaped last dose sleeve 110. The last dose sleeve 110 comprises a radially outwardly extending distal flange 111 extending on a distal end thereof. With this distal flange 111 the last dose sleeve 110 abuts in distal direction with a radially inwardly extending socket 24 of the housing 20. Moreover, by means of the distal flange 111 the last dose sleeve is also radially guided and confined in the proximal receptacle 23 of the housing 20.

Furthermore, by means of its flange portion 32 the actuation member 30 may be snapped on the proximal end of the housing 20 and may therefore positively engage with the housing 20 at least in proximal direction 2. In particular, the actuation member 30 is cup-shaped and surrounds and closes the receptacle 23 of the housing 20 in proximal direction when assembled thereon.

From a proximal portion of the last dose sleeve 110, there extend two helically shaped resilient spring elements 116 integrally formed with the last dose sleeve 110. These spring elements 116 abut with a proximal and inward facing portion of the hollow actuation member 30 and therefore keep the actuation member 30 in its initial, hence proximally located configuration as illustrated for instance in FIG. 8a.

In this initial configuration which coincides with and specifies a dose setting mode of the drive mechanism 3, axially inwardly extending journals 33 of the actuation member 30 extend into two respective diametrically oppositely located recesses 115 of a proximal rim 117 of the last dose sleeve 110. In this way, the last dose sleeve 110 and the actuation member 30 are rotatably coupled in the initial configuration of the actuation member 30 as shown in FIG. 8a as well as in the depressed configuration as shown in FIG. 8b.

In the initial configuration, rotation of the actuation member 30 leads to a corresponding rotation of the last dose sleeve 110. In the dose setting mode, the last dose sleeve 110 is further rotatably engaged and rotatably coupled with a clutch 40 as becomes apparent from a combination of FIGS. 4, 5*b* and 8*a*. As in particular illustrated in the cross section B-B in FIG. 5B, the inside facing portion of the distal end of the last dose sleeve 110 comprises a toothed surface 118 that meshes with radially outwardly extending teeth 45 of the clutch 40.

This way, the last dose sleeve 110 and the clutch 40 extending there through and hence providing an axis of rotation for the last dose sleeve 110, are rotatably fixed and are therefore rotatably engaged. Consequently, a rotation of the actuation member 30 leads to an equal rotation of the clutch 40 during a dose setting procedure. The clutch 40 is further connected with the drive sleeve 50. Hence, a distal portion of the clutch 40 is located inside the tubular shaped and hollow drive sleeve 50.

Here, and independent of the mode of operation of the drive mechanism 3, the clutch 40 and the drive sleeve 50 are axially fixed as well as rotatably fixed with respect to each other. Hence, a rotation of the clutch 40 is unalteredly transferred to the drive sleeve 50. Accordingly, also an axial displacement of the clutch 40 is unalteredly transferred to a respective axial displacement of the drive sleeve 50.

Figure 10A:
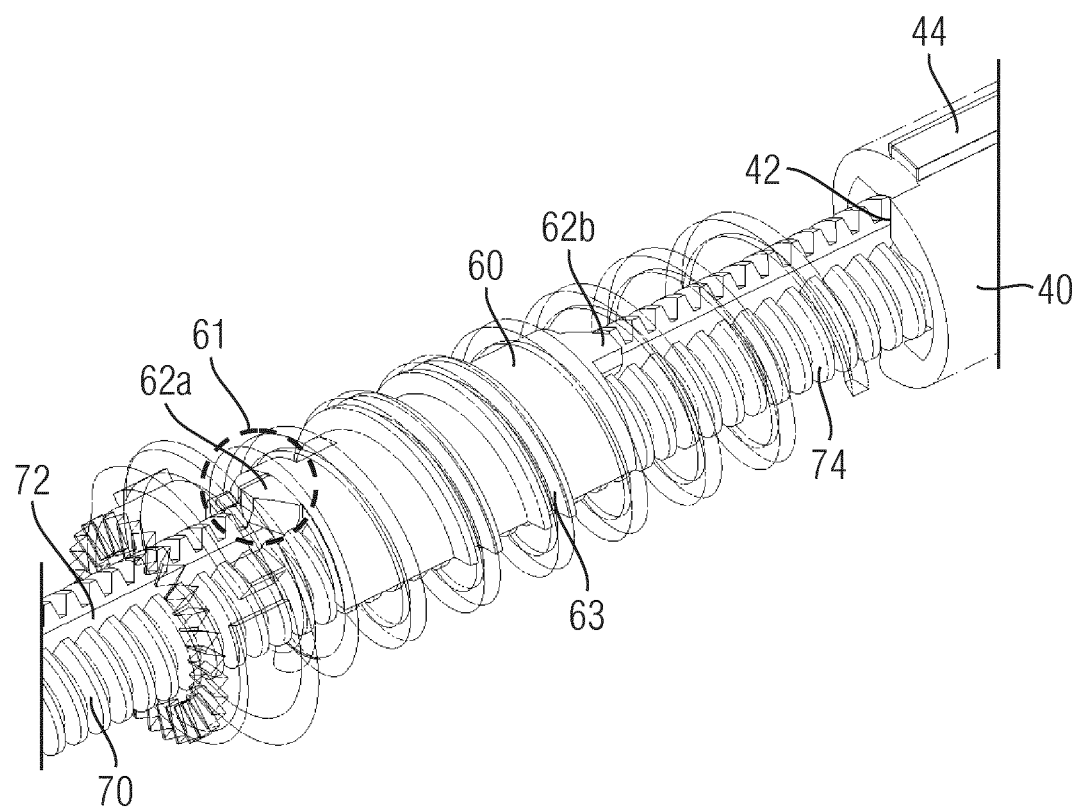
FIG. 10a shows the dose limiting member located on the piston rod in an isolated view.
Figure 10B:
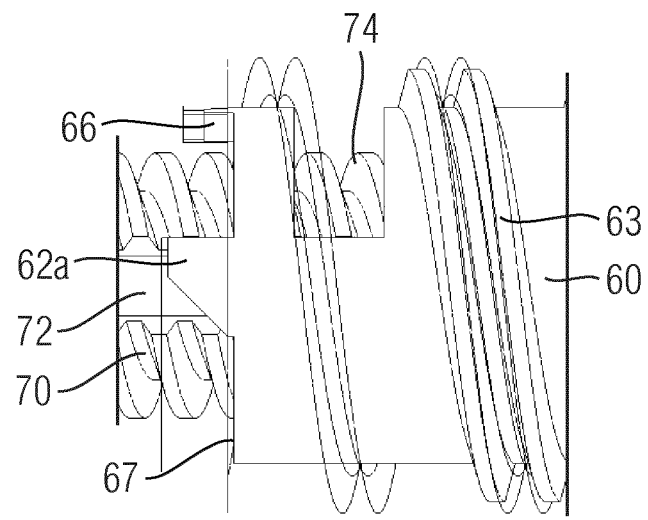
FIG. 10b shows an enlarged view of a distal end of the dose limiting member.
Figure 13:
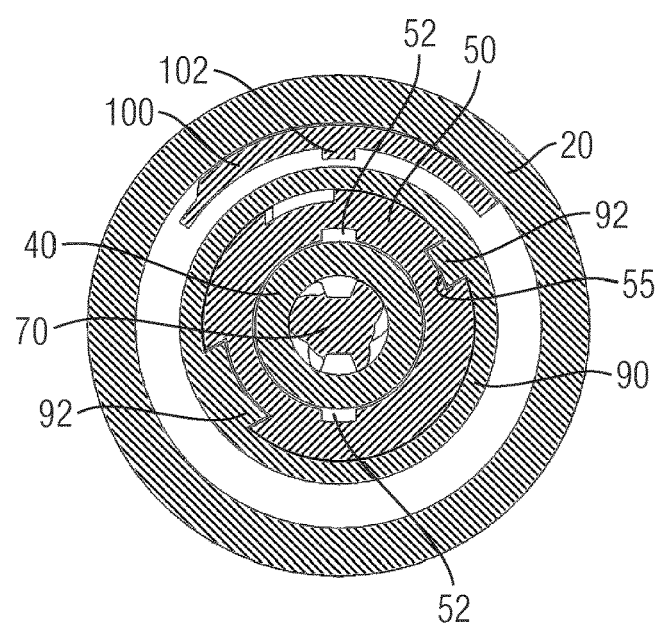
FIG. 13 shows a cross section F-F according to FIG. 4, FIG. 14 perspectively illustrates a dose limiting configuration, wherein the proximal stop portion of the dose limiting member engages with a distal stop of the clutch.
Figure 14:
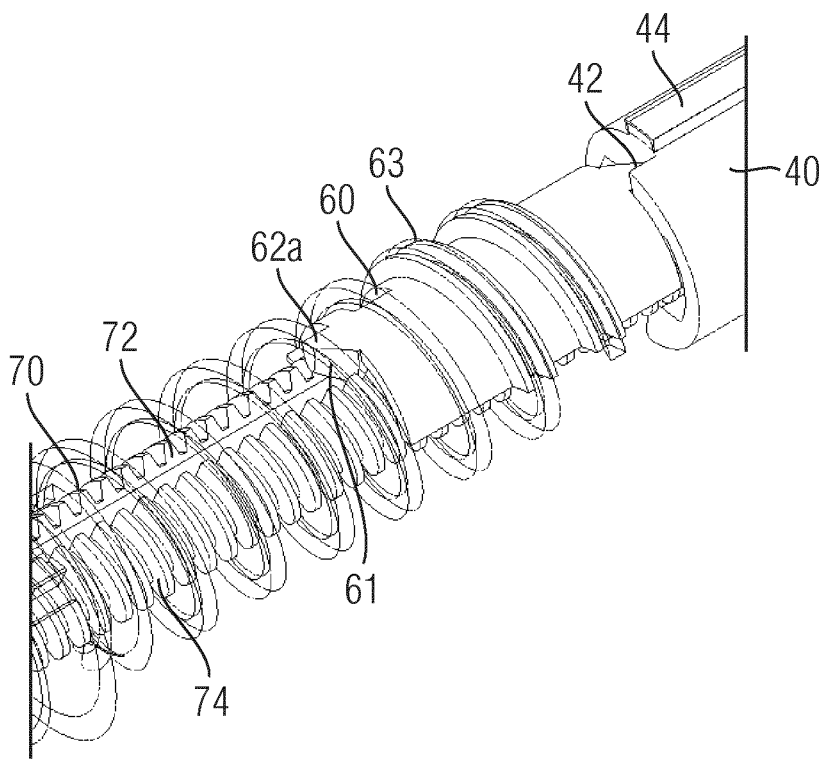
Figure 15:
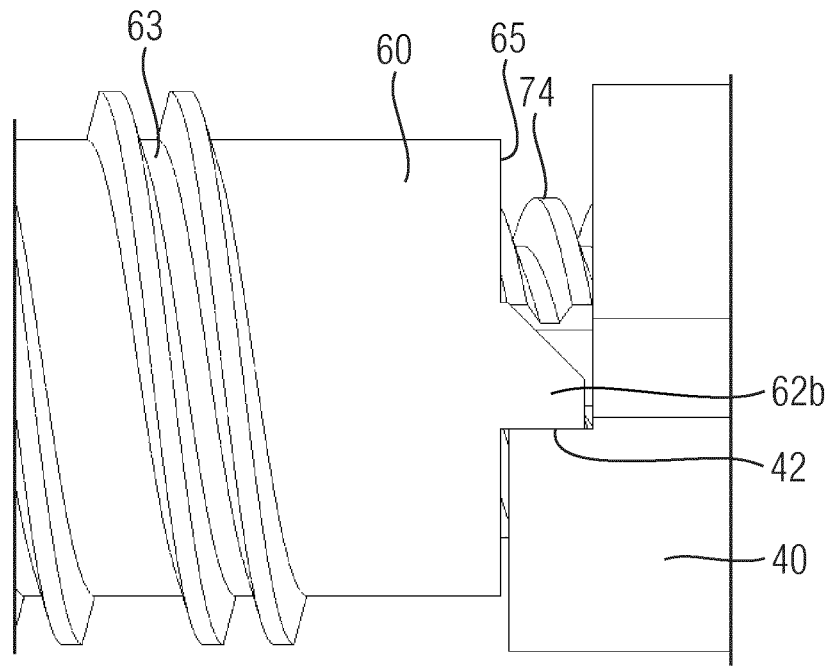
FIG. 15 shows a side view of mutually engaging dose limiting member and clutch according to FIG. 14, FIG. 16a schematically illustrates implementation of a last dose limiting mechanism in an initial configuration

The drive sleeve as indicated in FIG. 13 comprises two diametrically opposite longitudinal grooves 52 in its inside facing sidewall, as shown in FIG. 13, that are adapted to mate and to receive correspondingly shaped and radially outwardly extending ribs 44 of the clutch 40, as for instance indicated in FIGS. 10*a* and 14.

Figure 1:
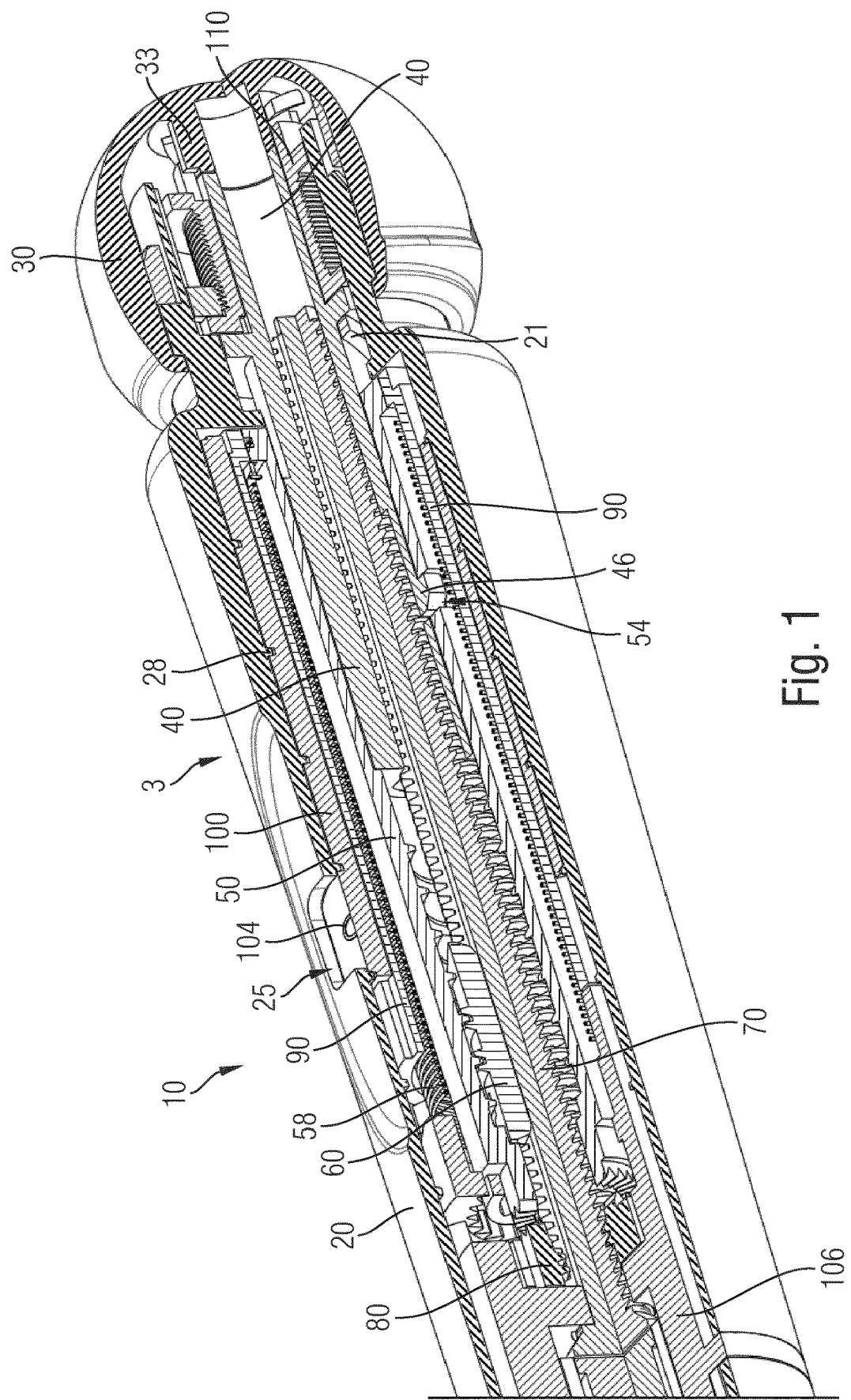
FIG. 1 schematically illustrates the assembled drive mechanism in a partially cut perspective view.

Moreover, the clutch 40 comprises at least one, preferably at least two oppositely located radially outwardly extending and resiliently deformable snap portions 46 adapted to engage with a correspondingly shaped recess 54 of the drive sleeve 50 as schematically illustrated in FIG. 1. By means of the mutually corresponding ribs 44 and grooves 52 as well as due to the snap portions 46 engaged with the recess 54, a rotational and longitudinal engagement of clutch 40 and drive sleeve 50 can be attained.

The drive sleeve 50 can be rotated inside and relative to the housing 20 in a dose incrementing direction against the action of a helical spring 58. One end, e.g. the proximal end of the helical spring 58 is attached and coupled to the proximal end of the drive sleeve 50 while an opposite, e.g. a distal end of the helical spring 58 is fastened to the housing 20. A dose incrementing rotation of the actuation member 30 therefore leads to a corresponding rotation of the drive sleeve 50 against the restoring force of the helical spring 58 almost completely surrounding the drive sleeve 50.

The drive sleeve 50 further comprises an arc-shaped ratchet member 51 near a distal end thereof. The ratchet member 51 is resiliently deformable in radial direction and comprises a radially outwardly extending tooth or nose 53 mating with a correspondingly shaped toothed profile 108 of an insert 106 located inside and fix to the housing 20.

In this context it is to be noted, that the insert 106 could also be integrally formed with the housing 20. It is predominately due to the assembly and manufacturing process that the insert 106 is provided as a separate part to be assembled in the housing 20. Hence, any reference made herein to the insert is equivalently valid for the housing and vice versa.

Figure 6A:
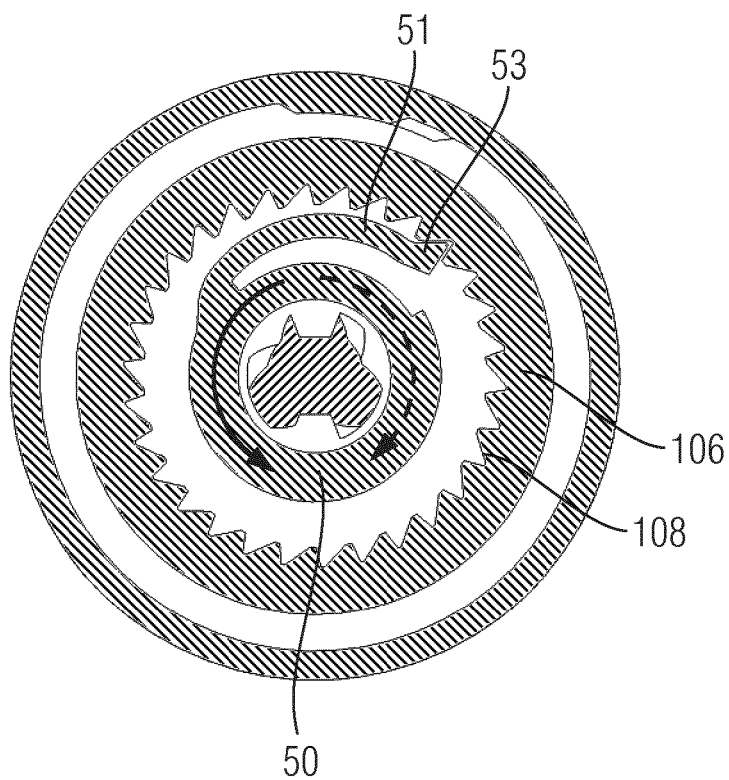
FIG. 6a shows a cross section through C-C according to FIG. 4.
Figure 6B:
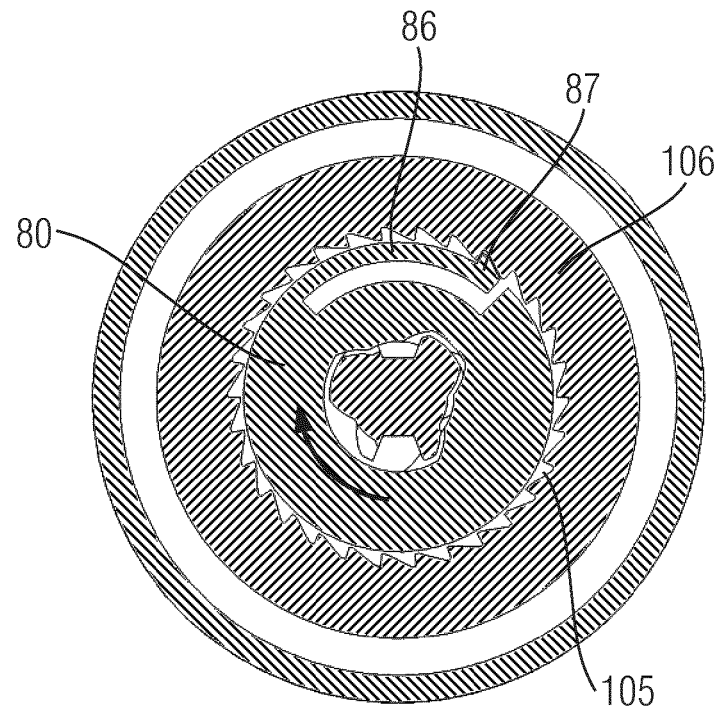
FIG. 6b shows a cross section D-D according to FIG. 4, FIG. 7a schematically shows the position of the drive sleeve relative to the drive nut during a dose setting procedure.

As indicated in the cross section C-C according to FIG. 6*a*, the tooth 53 provided at a free end of the resiliently deformable ratchet member 51 meshes with the toothed surface 108 of the insert 106 when rotating counter clockwise, hence during a dose incrementing rotation of the drive sleeve 50. Here, passing of the tooth 53 along the toothed surface 108 generates an audible feedback to the user, indicating, that the dose is stepwise incremented.

The geometry of the toothed surface 108 and the tooth 53 is designed such, that the spring force arising from the helical spring 58 and acting in opposite, hence clockwise direction on the drive sleeve 50 is not large enough to rotate the drive sleeve 50 in the opposite, hence clockwise sense. This way, mechanical energy can be stored by the helical spring 58 which is to be released only on demand during a subsequent dose dispensing procedure.

Even though not particularly illustrated here, the toothed surface 108 and the ratchet member 51 engage in such a way, that a dose decrementing rotation of the drive sleeve 50 is indeed possible, e.g., when a user exerts a respective counter-directed angular momentum to the actuation member 30, which exceeds the resilient resistance provided by the mutually engaged ratchet member 51 and the toothed surface 108.

A dose incrementing action governed by a rotation of the actuation member 30 and a corresponding rotation of the drive sleeve 50 also leads to a corresponding rotation of a dose indicating sleeve 100. The dose indicating sleeve 100 is threadedly engaged with the housing 20 and comprises numerous dose indicating numbers 104 at its outer circumference, as for instance indicated in FIG. 3. The numbers are arranged in a helical way on the outer circumference of the dose indicating sleeve 100. Moreover, the dose indicating sleeve 100 is threadedly engaged with the inside facing sidewall portion of the housing 20 as becomes apparent from the inner thread 28 of the housing 20 as for instance indicated in FIG. 1.

A rotation of the drive sleeve 50 unalteredly transfers to a respective rotation of the dose indicating sleeve 100 via the engagement of an intermediate sleeve 90. The intermediate sleeve 90 is sandwiched in radial direction between the drive sleeve 50 and the dose indicating sleeve 100. Hence, the intermediate sleeve 90 surrounds the drive sleeve 50 and is further rotatably coupled with the drive sleeve 50 at a proximal end portion as indicated in FIG. 13. As illustrated there, the drive sleeve 50 is splined to the intermediate sleeve 90. The drive sleeve 50 comprises two oppositely disposed radially inwardly extending recesses 55 to receive correspondingly shaped radially inwardly extending protrusions 92 of the intermediate sleeve 90.

Figure 12:
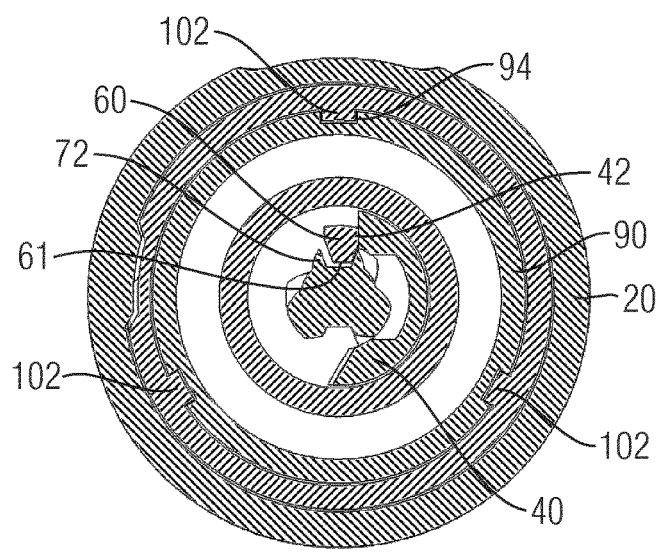

As indicated further in the cross section according to FIG. 12 the intermediate sleeve 90 is also splined with its outer circumference to the dose indicating sleeve 100. Hence, the intermediate sleeve 90 comprises three circumferentially distributed and radially inwardly extending recesses 94 as its outer circumference to receive correspondingly shaped and radially inwardly extending protrusions 102 of the dose indicating sleeve 100. The dose indicating sleeve 100 is threadedly engaged with the housing 20 and is therefore axially engaged with respect to the housing. However, the splined engagement of the intermediate sleeve 90 with the dose indicating sleeve 100 allows for an at least limited sliding axial displacement between the dose indicating sleeve 100 and the intermediate sleeve 90, in particular during a mode switching of the drive mechanism 3.

Since the intermediate sleeve 90 may be axially displaceable relative to the dose indicating sleeve 100 intermediate sleeve 90 and drive sleeve 50 could also be integrally formed, thereby reducing the number of parts and components the drive mechanism is made of.

When during a dose setting procedure the actuation member 30 is rotated relative to the housing the drive sleeve 50 is rotated in the same way and due to the two-fold splined engagement of drive sleeve 50, intermediate sleeve 90 and dose indicating sleeve 100 also the dose indicating sleeve 100 will always instantly show a corresponding dose size indicating number 104, e.g. representing an amount of international units (I.U.) in a dose displaying window 25 of the housing 20. As indicated for instance in FIG. 9, the dose indicating window 25 may comprise a recess or a through opening in the sidewall of the housing 20.

Decrementing of the dose, hence dialing the actuation member 30 in an opposite sense of rotation, leads to a respective counter-rotation of the drive sleeve 50. Consequently, also the intermediate sleeve 90 and the dose indicating sleeve 100 rotate in the opposite sense and a correspondingly decreasing dose indicating number will show up in the window 25.

In an alternative embodiment, the inner thread 28 of the housing 20 may only be provided at a portion of the inside facing sidewall of the housing 20 which is located proximal from the dose indicating window 25. Said housing portion proximally offset from the dose indicating window 25 may either comprise a positive or negative threaded portion. Hence, it may either comprise a helically extending groove or a radially inwardly extending helically extending protrusion. As a consequence, the dose indicating sleeve only has to provide a correspondingly shaped threaded portion at its proximal end. In this way, a distal portion of the dose indicating sleeve may be free of threads, grooves or protrusions.

In the following dispensing of a dose is described.

Once a dose has been correctly set, the drive mechanism 3 may be switched into a dispensing mode by depressing the actuation member 30 in distal direction 1 as for instance indicated in FIG. 8b. Hence, the actuation member 30 fulfils a double or even a triple function. First of all, the actuation member 30 serves to transfer an angular momentum to the last dose sleeve 110 and/or to further functional components of the drive mechanism 3 operably engaged therewith. Second, the actuation member 30 controls and triggers a dose dispensing procedure. Third, the actuation member 30 actually seals and closes a proximal end of the housing 20 of the drive mechanism 3 and/or of the drug delivery device 10.

Moreover, the present arrangement of the actuation member 30 also allows for a priming of the drive mechanism 3 during manufacturing of the drug delivery device 10, when a cartridge 14 is to be readily arranged therein. In the process of assembly of the device 10, the piston rod 70 can be advanced in distal direction 1 to directly abut with the piston 16 of the cartridge 14. Here, a proximal end of the piston rod 70 is accessible, e.g. by means of a separate push rod, which is actually not illustrated here. It is then after bringing the piston rod 70 in operative engagement with the piston 16 of the cartridge 14 that the actuation member 30 is finally assembled to the housing 20 thereby closing the proximal receptacle 23 thereof.

By displacing the actuation member 30 in distal direction 1, the resilient spring elements 116 of the last dose sleeve 110 will be compressed. At the same time, the axially inwardly protruding journals 33 of the actuation member 30 will further extend through the longitudinal recesses 115 of the last dose sleeve 110 and will push a proximal rim 48 of the clutch 40 in distal direction 1 as becomes apparent from a comparison of FIGS. 8a and 8b.

Figure 5A:
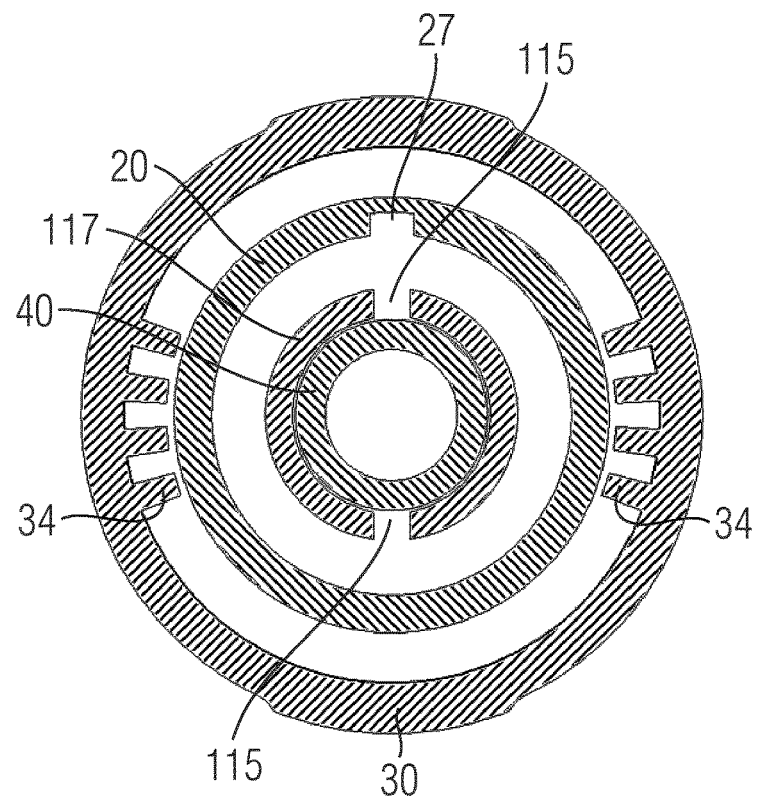
FIG. 5a shows a cross section along A-A of FIG. 4.
Figure 5B:
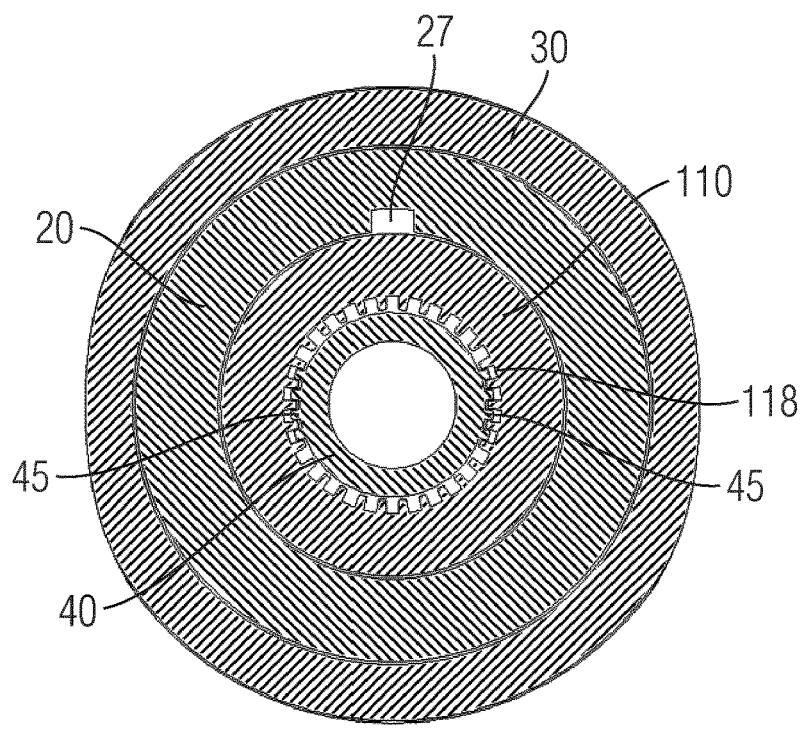
FIG. 5b shows a cross section along B-B according to FIG. 4.

Due to this distally directed displacement of the clutch 40, radially outwardly extending teeth 45 of the clutch 40, as shown in FIG. 5b, do no longer engage with the inner toothed surface 118 of the last dose sleeve 110. As a consequence, the clutch 40 is rotatably disengaged from the last dose sleeve 110 and is free to rotate.

At the same time radially inwardly extending teeth 34 provided at the inside facing sidewall portion of the actuation member 30 engage with a toothed ring 26 provided on the outer circumference of the proximal portion of the housing 20. Since the teeth 34 get in engagement with the toothed ring 26 by the axial and distally directed displacement of the actuation member 30 relative to housing 20, the actuation member 30 is rotatably locked to the housing 20 during a dose dispensing action. Consequently, the last dose sleeve 110, which is still rotatably engaged with the actuation member 30, cannot rotate during the dose dispensing procedure.

Since the clutch 40 is not only rotatably but also axially coupled and connected with the drive sleeve 50, the distally directed displacement of the clutch 40 is substantially unalteredly transferred to a respective distally directed displacement of the drive sleeve 50.

As further indicated in FIG. 1, the clutch 40 is biased in proximal direction 2 by means of at least one spring element 21, which is preferably integrally formed with the housing 20. The spring element 21 can be resiliently deformed and biased in axial, hence distal direction 1 by the radially extending flange 49 of the clutch 40. Since the clutch 40 is only to be displaced in distal direction 1 against the action of the spring element 21, the coupling of the drive sleeve 50 with a drive nut 80 is only active as long as a respective distally directed force is applied to the actuation member 30, e.g. during a dose dispensing procedure.

Figure 7A:
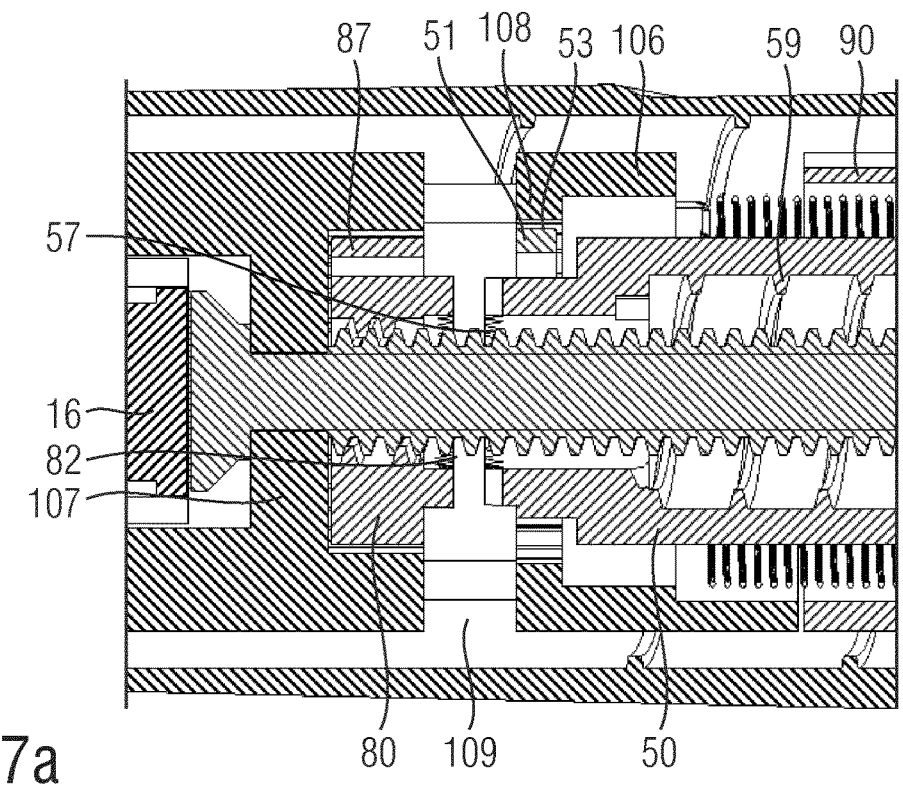
FIG. 7b shows an operable engagement of drive sleeve and drive nut during a dose dispensing procedure.
Figure 7B:
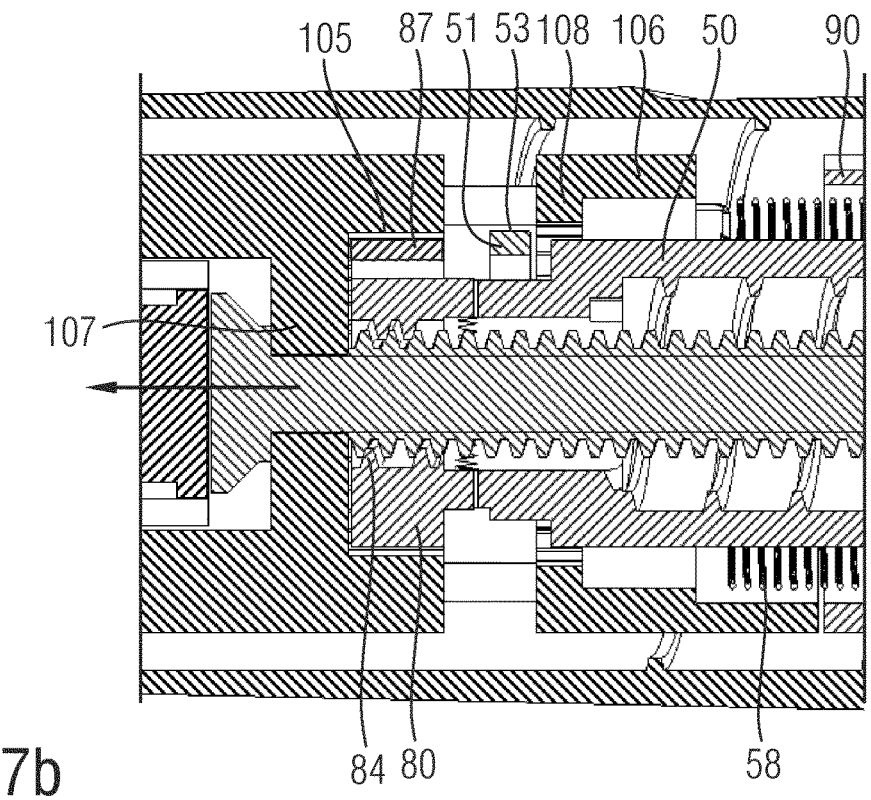

The distally directed displacement of the drive sleeve 50 is limited by the drive nut 80 as illustrated in cross section in FIGS. 7a and 7b. When in mutual axial abutment as indicated in FIG. 7b, the drive sleeve 50 and the drive nut 80 are rotatably engaged while the drive sleeve 50 and its ratchet member 51 is disengaged from the tooted surface 108 of the insert 106. Mutual rotatable engagement of drive sleeve 50 and drive nut 80 is achieved by mutually corresponding teeth or comparative interlocking members provided on a distal face 57 of the drive sleeve 50 and on a proximal end face 82 of the drive nut 80, respectively. The proximal end face 82 of the drive nut 80 may comprise a crown wheel operable to engage with a correspondingly shaped crown wheel provided on the distal face 57 of the drive sleeve 50.

Preferably, the axial extension of mutually corresponding crown wheels or spur gears located on the proximal face 82 and on the distal face 57 is such, that a rotational engagement of drive sleeve 50 and drive nut 80 is achieved before the ratchet member 51 of the drive sleeve 50 is released from the toothed surface 108 of the insert 106 during a distally directed displacement of the drive sleeve 50. In this way, a substantially slipless coupling of drive sleeve 50 and drive nut 80 can be achieved.

An early or premature release of the actuation member 30 prior to a termination of the dose dispensing procedure will lead to an immediate proximally directed displacement of the clutch 20 relative to the housing 20 under the effect of the biased spring element 21. Consequently, the ratchet member 51 of the drive sleeve 50 will reengage with the toothed surface 108 of the insert 106 for keeping the energy stored in the biased helical spring 58.

The drive nut 80 is preferably axially fixed in the insert 106. As indicated in FIGS. 7a and 7b, the insert 106 may comprise a circumferential or punctual recess 109 to receive an axially acting fastening member for the drive nut 80.

The insert 106 further comprises two diametrically oppositely arranged and radially inwardly extending protrusions 107 that engage with correspondingly shaped grooves 72 of the piston rod 70. The piston rod 70 extends through the insert 106 in axial direction and comprises a pressure foot 71 at its distal end to directly engage with the piston 16 of the cartridge 14. The radially inwardly extending protrusions 107 of the insert 106 may further be part of a web or flange portion featuring a through opening, through which the piston rod 70 extends axially. The pressure foot 71 may be rotatable with respect to the piston rod 70. But when the piston rod 70 is non-rotatably engaged with the housing 20, the rotatably supported pressure foot 71 is not required in general.

The piston rod 70 comprises an outer thread 74 which is only threadedly engaged with an inner thread 84 of the drive nut 80.

When rotatably coupled, the drive sleeve 50 under the action of the biased helical spring 58 transfers an angular momentum to the drive nut 80, which in turn rotates around the axially fixed piston rod 70. The rotation of the drive nut 80 then serves to advance the piston rod 70 in distal direction 1 for expelling of a dose of the medicament.

Moreover, in the distal stop position as illustrated in FIG. 7b, the ratchet member 51 of the drive sleeve 50 may audibly engage with another toothed inner surface of the insert 106 or housing 20, respectively which is located distally offset from the toothed surface 108. In this way a dose decrementing rotation of the drive sleeve 50 during dose dispensing may generate an audible feedback for the user that a dose dispensing procedure is actually in progress.

The drive nut 80 also comprises a ratchet member 86 having a circumferentially extending arm resiliently deformable in radial direction. At the free end of the ratchet member 86 a radially outwardly extending tooth 87 is located which is adapted to mesh with a correspondingly shaped toothed surface 105 provided at the inside facing wall of the insert 106. As indicated in cross section in FIG. 6b the ratchet member 86 and the toothed surface 105 are configured such, that only a clockwise, hence a dose dispensing rotation of the drive nut 80 is allowed while a counter-directed rotation of the drive nut 80 is effectively inhibited. This way, the piston rod 70 is only displaceable in distal direction 1 but not in proximal direction with respect to the housing 20. The ratchet member 86 of the drive nut 80 and the toothed surface 105 of the insert 106 provide an effective anti-backup feature.

Moreover, when rotating in a dose decrementing direction during a dose dispensing procedure, the ratchet member 86, and in particular its radially outwardly extending free end consecutively meshes with the geared or toothed profile of the insert 106 or with a correspondingly shaped inner surface portion of the housing 20. The mutual engagement of the ratchet member 86 sliding along the toothed surface 108 also generates an audible click sound inherently indicating to the user, that the dispensing procedure is actually in progress.

Also, implementation of the last dose sleeve 110 may be optional to the last dose limiting functionality provided by the interaction of the dose limiting member 60, the piston rod 70 and the drive sleeve 50.

Figure 17A:
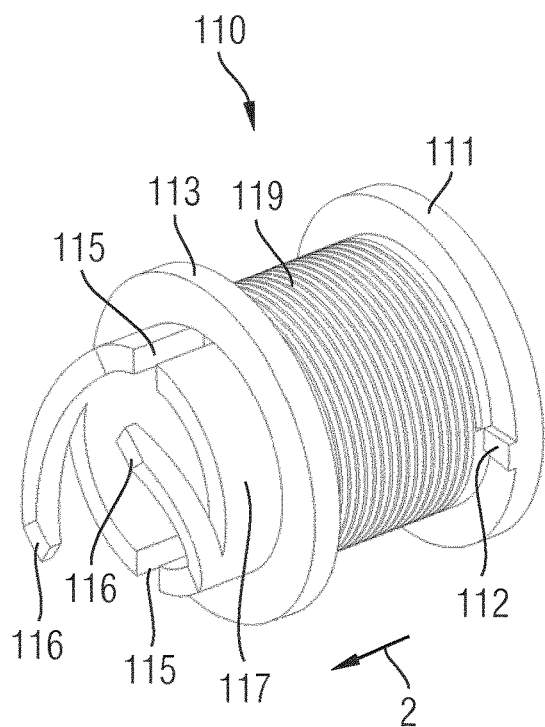
FIG. 17b shows the last dose sleeve with a last dose member assembled thereon.
Figure 17B:
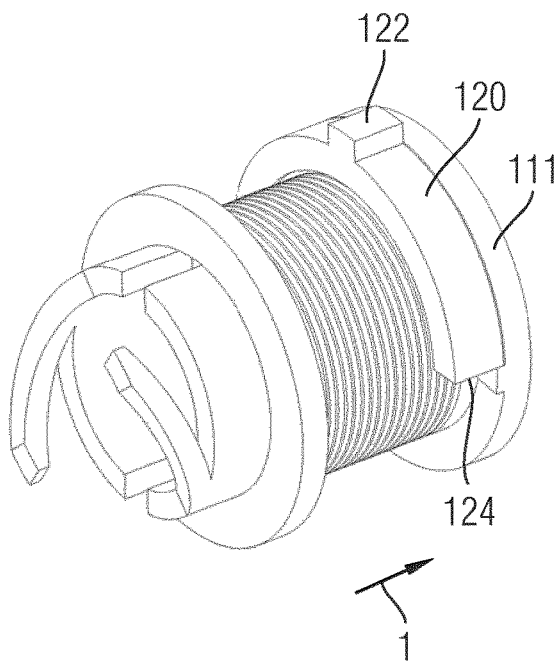
Figure 18A:
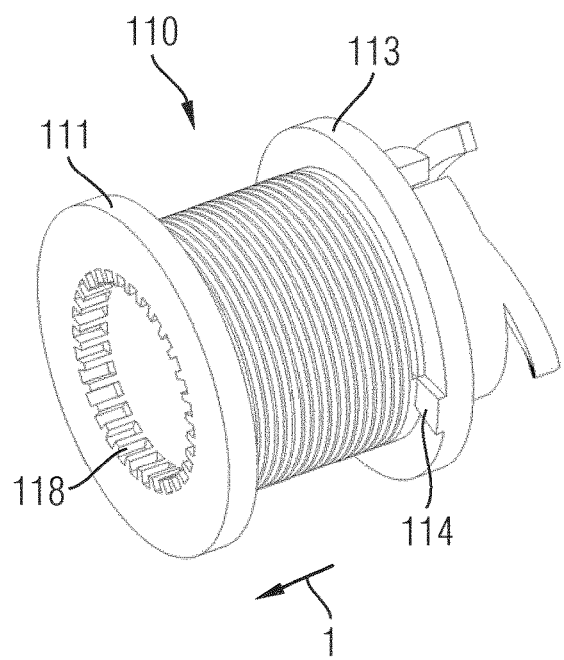
FIG. 18a shows an opposite perspective view of the last dose sleeve according to FIG. 17a and FIG. 18b shows a corresponding alternative perspective view of the last dose sleeve with the last dose member assembled thereon, FIG. 19 perspectively illustrates in a partially transparent view of the interaction of the dose limiting member and the drive sleeve during dose setting, FIG. 19a schematically shows an enlarged view of a framed section of FIG. 19, FIG. 20 schematically illustrates mutual interaction of the dose limiting member and the drive sleeve during dose dispensing
Figure 18B:
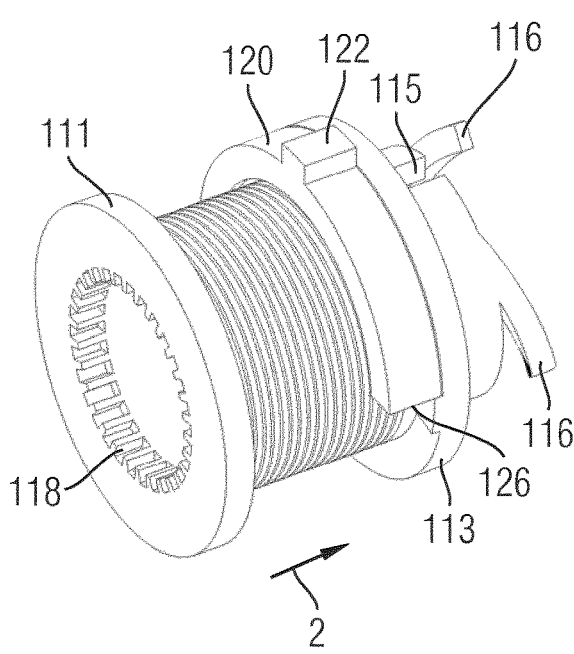

For providing a last-dose- or end-of-content mechanism, a last dose sleeve 110 as illustrated in FIGS. 8a through 8b and in FIGS. 17a to 18b is provided inside the actuation member 30. The last dose sleeve 110 comprises an outer thread 119 extending between a distal flange 111 and a proximal flange 113. The last dose sleeve 110 is further engaged, in particular threadedly engaged with a last dose member 120, which is of annular or arc-shape as illustrated in FIGS. 17b and 18b. The last dose member 120 comprises an internal thread 128 to threadedly engage with the outer thread 119 of the last dose sleeve 110 and further comprises a radially outwardly extending protrusion 122 engaged with an axially extending groove 27 provided on the inside facing sidewall of the proximal receptacle 23 of the housing 20.

The groove 27 is also illustrated in the cross section A-A in FIGS. 5a and 5b. Since the protrusion 122 of the last dose member 120 engages with the groove 27 of the housing 20, the last dose member is rotatably locked to the housing 20 and is therefore hindered to rotate with respect to the housing 20 in circumferential direction. Due to its threaded engagement with the outer thread 119 of the last dose sleeve 110, the last dose member is displaced in axial direction 1 when the last dose sleeve 110 is rotated with respect to the housing 20.

Typically, the last dose member 120 comprises a leading edge 124 and a trailing edge 126 in circumferential direction with respect to the sense of rotation of the last dose sleeve 110 relative to the last dose member 120. By means of its leading and/or trailing edges 124, 126, the last dose member 120 is engageable with the radially extending or radially protruding stop 112 or 114 provided on the outer circumference of the last dose sleeve 110 when reaching a last dose limiting configuration.

When the leading or trailing edge 124, 126 of the last dose member 120 abuts or engages with the at least one stop 112, 114 of the last dose sleeve 110, further rotation of the last dose sleeve 110 can be effectively blocked and inhibited, thereby blocking or inhibiting a further dose incrementing rotation of the actuation member 30 during a dose setting procedure. The radially and preferably also axially extending leading or trailing edge 124, 126 of the last dose member 120 and the correspondingly shaped stop 112, 114 of the last dose sleeve 110 are adapted to immediately block a further rotation of the last dose sleeve 110 and hence of the actuation member 30 when a predetermined rotational position of the last dose sleeve 110 and the actuation member 30 has been reached.

The thread 119 and the axial dimensions of the last dose sleeve 110 are selected such, that an axial position of the last dose member 120 on the last dose sleeve 110 is directly correlated to the axial position of the piston rod 70 and hence to the axial position of the piston 16 in the cartridge 14.

The last dose sleeve 110 further comprises a distal stop 112 extending radially outwardly from the distal end of the thread 119 as illustrated in FIG. 17a. As soon as a leading edge 124 of the last dose member 120 abuts with the distal stop 112 of the last dose sleeve 110 a further rotation of the last dose sleeve 110 with respect to the housing 20 and may be effectively blocked. In this way, setting of a dose exceeding the filling level or the amount of medicament contained in the cartridge 12 can be effectively prevented.

The last dose sleeve 110 also comprises a proximal stop 114 as indicated in FIG. 18a. The proximal stop 114 provides a well-defined position for the last dose member 120 in an initial device configuration and for assembly of the drug delivery device and its drive mechanism 3. Here, the radially extending flange portions 111, 113 of the last dose sleeve 110 also provide a support structure for the distal stop 112 and for the proximal stop 114 both extending in radial direction from the external thread 119 of the dose sleeve 110.

It is to be mentioned here, that the last dose limiting mechanism implemented by the last dose sleeve 110 is beneficial in that the last dose sleeve 110 is directly located inside the actuation member 30. In effect, a tolerance chain between the actuation member 30 and the last dose limiting mechanism is fairly short and can therefore be reduced to a minimum.

Moreover, the flexibility of the various parts of which the drive mechanism 3 is assembled may play a subordinate role, as the flux of force from the actuation member 30 to the last dose sleeve 110 is comparatively short. Moreover, also from a user's point of view, the position of the last dose sleeve 110 together with the last dose member 120 inside the actuation member 30 will provide a rather solid, robust and therefore very reliable last dose limiting mechanism.

The drive mechanism 3 may further and optionally comprise another, single dose limiting mechanism, e.g. for limiting a dose setting as well as a dose dispensing procedure. Here, the drive mechanism 3 further comprises a dose limiting member 60 slideably arranged on the piston rod 70 in axial direction and threadedly engaged with the drive sleeve 50. The dose limiting member 60 comprises the shape of a half-shell and therefore only partially surrounds the piston rod 70 in circumferential or tangential direction. The dose limiting member 60 comprises a radially inwardly extending gliding portion 61 by way of which the dose limiting member 60 may slide or glide along the groove 72 of the piston rod 70. Due to the this mutual engagement of the gliding portion 61 and the groove 72 of the piston rod 70, the dose limiting member 60 is rotatably fixed to the piston rod 70. In other words the dose limiting member 60 is splined to the piston rod 70 or is keyed engaged with the piston rod 70.

The dose limiting member 60 further comprises an external thread 63 at its outer circumference to engage with a correspondingly shaped internal thread 59 of the drive sleeve 50. In this way, the dose limiting member 60 is displaced axially with respect to the piston rod 70 as well as with respect to the drive sleeve 50 when the drive sleeve 50 rotates relative to the piston rod 70, in particular during a dose setting procedure.

During such a dose dispensing procedure, the drive sleeve 50 rotates in an opposite direction and hence the dose limiting member 70 experiences an oppositely directed axial displacement relative to the piston rod 70 and relative to the drive sleeve 50.

Typically, during a dose setting procedure, the dose limiting member is displaced in proximal direction 2 towards the clutch 40. During a dose dispensing procedure, the dose limiting member 60 is displaced in the opposite direction, hence in distal direction 1 towards the drive nut 80.

At its proximal end the dose limiting member 60 comprises a proximal stop portion 62b extending from a proximal end face 65 of the dose limiting member 60 in axial, hence proximal direction 2.

The proximal stop portion 62b is adapted to abut with a correspondingly shaped and correspondingly oriented radially extending stop 42 provided at a distal end of the clutch 40. Such an abutment configuration is for instance shown in FIGS. 14 and 15. By means of the mutual abutment of the proximal stop portion 62 of the dose limiting member 60 with the stop 42 located at the distal end of the clutch 40, a further rotation of the drive sleeve 50 as well as of the clutch 40 relative to the piston rod 70 can be effectively inhibited.

Since the proximal stop portion 62b of the dose limiting member 60 abuts in radial and circumferential direction with the clutch 40, any further rotation of the clutch 40 and hence any further rotation of the drive sleeve 50 rotatably coupled therewith is effectively blocked. Moreover, the clutch 40 also provides a proximal stop for the dose limiting member 60. Due to the threaded engagement of the dose limiting member 60 and the drive sleeve 50, also here, a further rotation of the drive sleeve 50 exceeding a predefined maximum single dose configuration can be prevented. In this way, the dose limiting member 60 serves to provide a single dose limiting mechanism which is operable to effectively inhibit setting of a dose exceeding a predefined maximum single dose, e.g. 120 I.U. of insulin.

Figure 11:
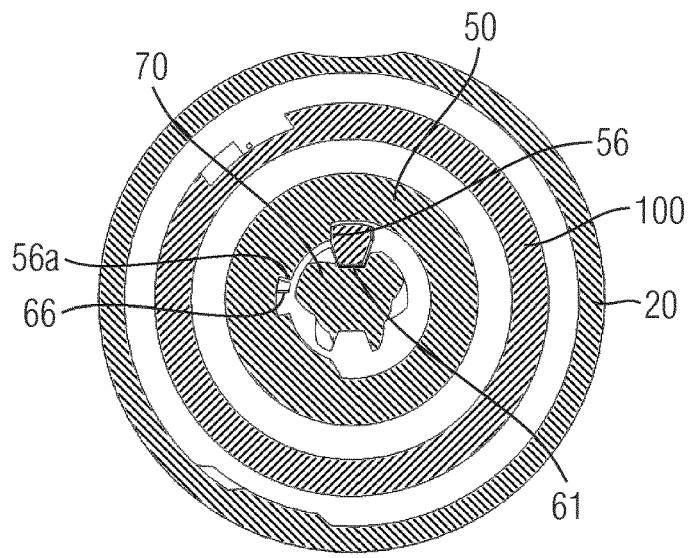
FIG. 11 is a cross section along E-E according to FIG. 4, FIG. 12 schematically illustrates a cross section through the drive mechanism when the dose limiting member engages and radially abuts with the clutch.

The dose limiting member 60 also comprises a distal stop portion 62a extending accordingly in distal direction 1 from a distal end face 67 of the dose limiting member 60. Here, the distal stop portion 62a may accordingly engage with a radially inwardly and axially extending stop 56 of the drive sleeve 50. The corresponding distal stop 56 of the drive sleeve is apparent from FIGS. 19a and 20a. Additionally, the radially inwardly and axially extending stop 56 of the drive sleeve 50 is shown in FIG. 11 in an abutment configuration with the dose limiting member 60.

The position and orientation of the distal stop portion 62a and the stop 56 is selected such, that a mutual abutment of distal stop portion 62a and stop 56 is correlated with a zero dose configuration at the end of a dose dispensing procedure, i.e. when the dose indicating sleeve 100 has returned into its initial position.

Since the rotation of the drive sleeve 50 can be blocked and interrupted by the dose limiting member 60 in both directions, i.e. in a dose setting mode as well as in a dose dispensing mode, further stop features to inhibit a dose incrementing or dose decrementing rotation of the drive sleeve 50 are generally not required. As a consequence, even the dose indicating sleeve 100 and its arrangement in the housing 20 can be provided without any further rotation limiting means.

As shown in FIGS. 10b and 19 to 20a, the distal stop portion 62a of the dose limiting member 60 is further equipped with a clicking member 64 which is adapted to generate an audible sound before or when the distal stop portion 62a engages with the stop 56 of the drive sleeve 50. The clicking member 64 comprises a resilient arm 68 extending in circumferential direction from the distal stop portion 62a. At its free end the arm 68 comprises a latch portion 66 featuring a tooth-like shape with a slanted or tilted leading surface. During a dose dispensing procedure and well before reaching the distal stop configuration, the latch portion 66 engages with the stop 56 and becomes subject to a axially, hence proximally directed evasive movement due to the resilient deformability of the arm 68.

Figure 20:
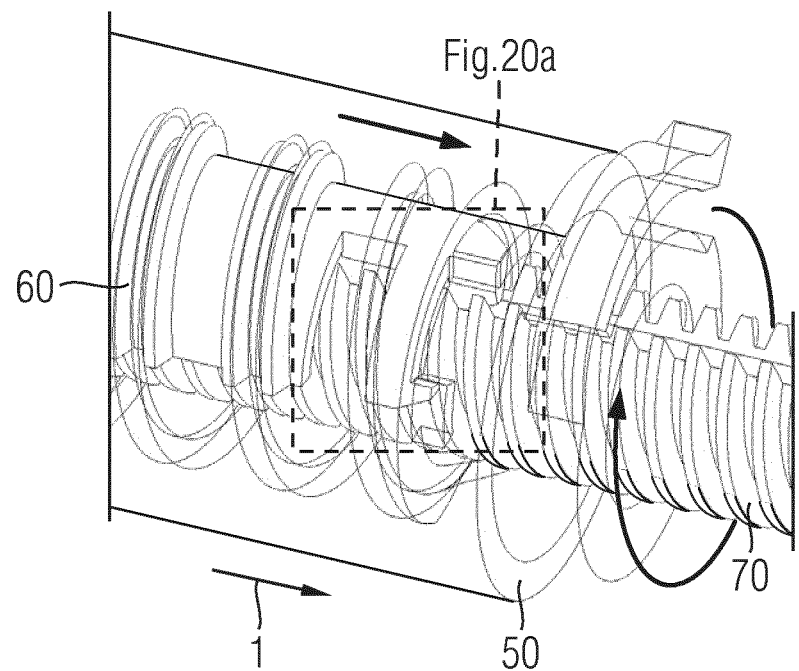
FIG. 20a shows an enlarged framed section of FIG. 20.
Figure 20A:
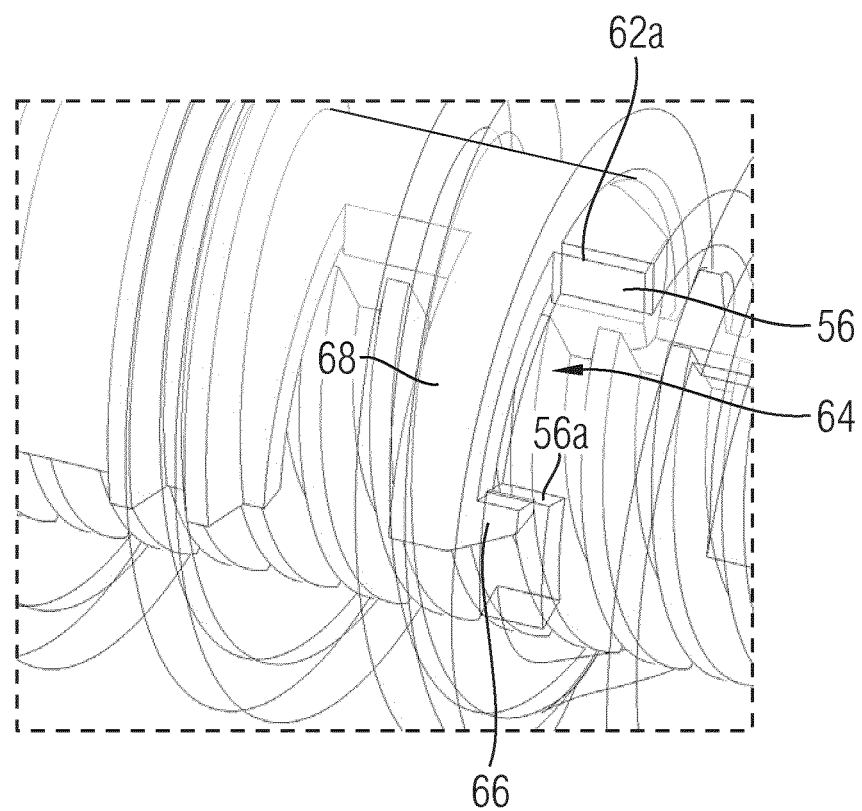

In the final stop configuration as indicated in FIGS. 20 and 20a, the latch portion 66 may relax and may snap into a recess 56a provided at the inside wall of the drive sleeve 50, thereby generating an audible click sound. The returning of the latch portion 66 and the resilient arm 68 into its initial unbiased configuration may occur before the distal stop portion 62a engages with the stop 56 or it may coincide with the stop configuration, thereby audibly indicating to a user, that the dose dispensing procedure is close to end or has just terminated. Said audible feedback is not only obtained at the end of a dose dispensing procedure but also when a zero dose size, e.g. 0 I.U., is set by means of a dose correction procedure.

Figure 19:
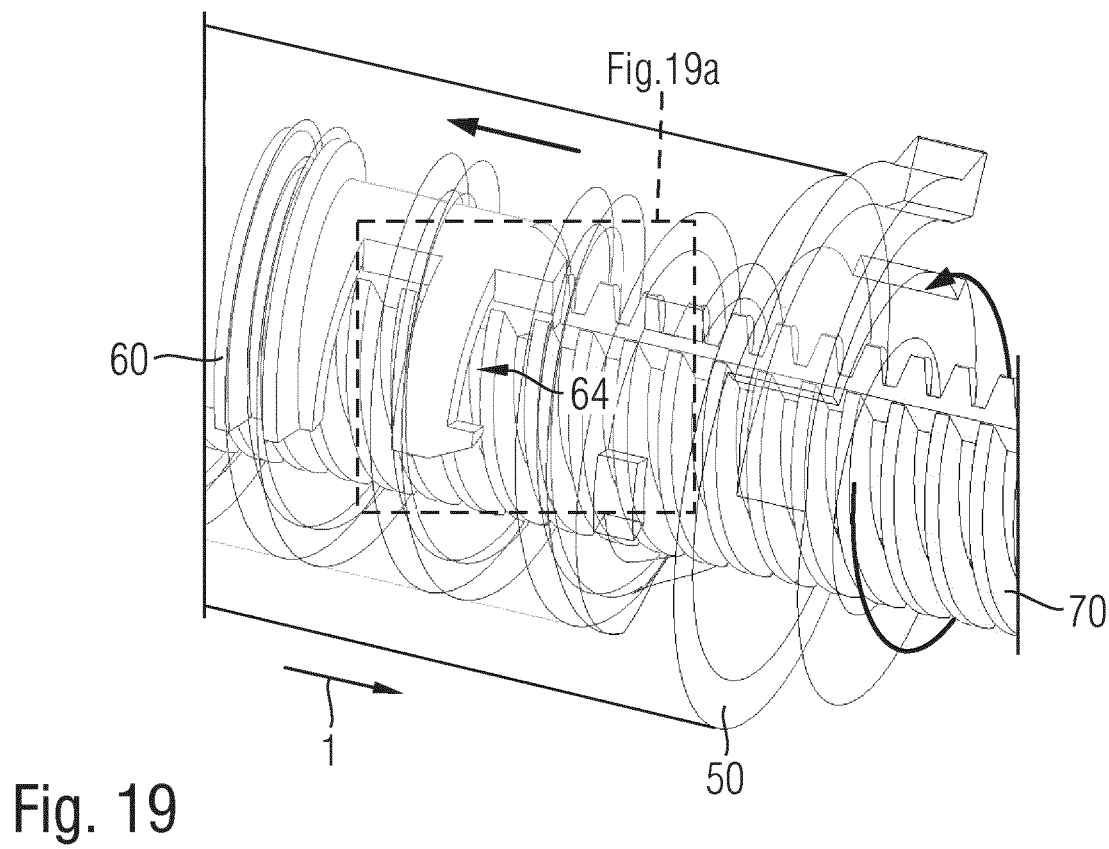
Figure 19A:
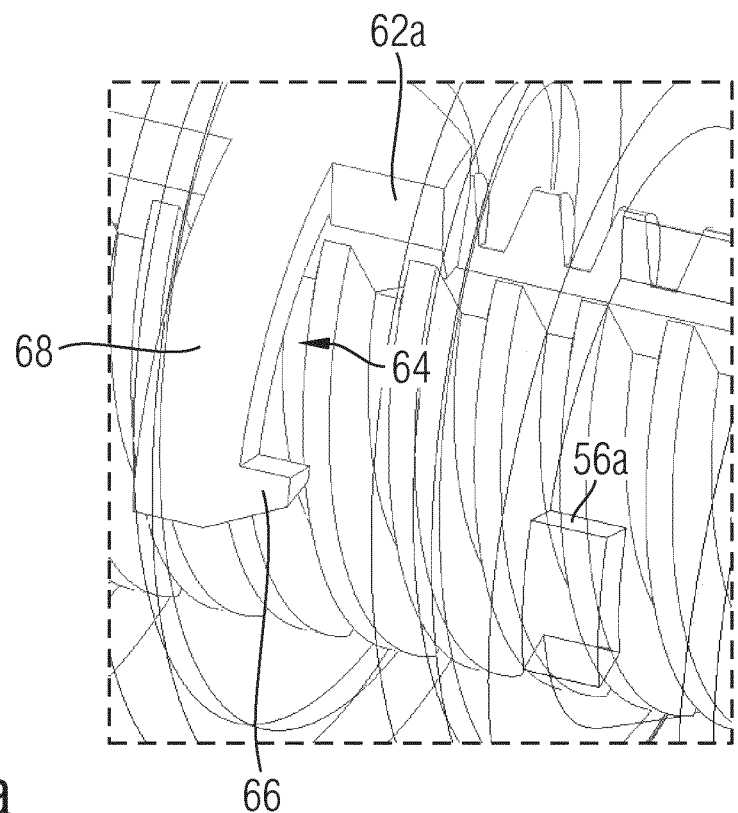

In FIGS. 19 and 19a, the stop 56 and the circumferentially offset recess 56a are illustrated after the dose limiting member 60 has been displaced in proximal direction 2. It is apparent from FIGS. 19a and 20a as well as from FIG. 10b, that the distal stop portion 62a axially protrudes from the axial end of the latch portion 66. Since the axial height of the latch portion 66 is slightly smaller than that of the trailing distal stop portion 62*a*, the latch portion 66 and the clicking member 64 does not substantially affect the operability of the drive mechanism. The cross section E-E according to FIG. 11 further illustrates the coincidence of the latch portion 66 engaging with the recess 56*a* and the distal stop portion 62*a* engaging with the stop 56 of the drive sleeve 50.

Figure 16A:
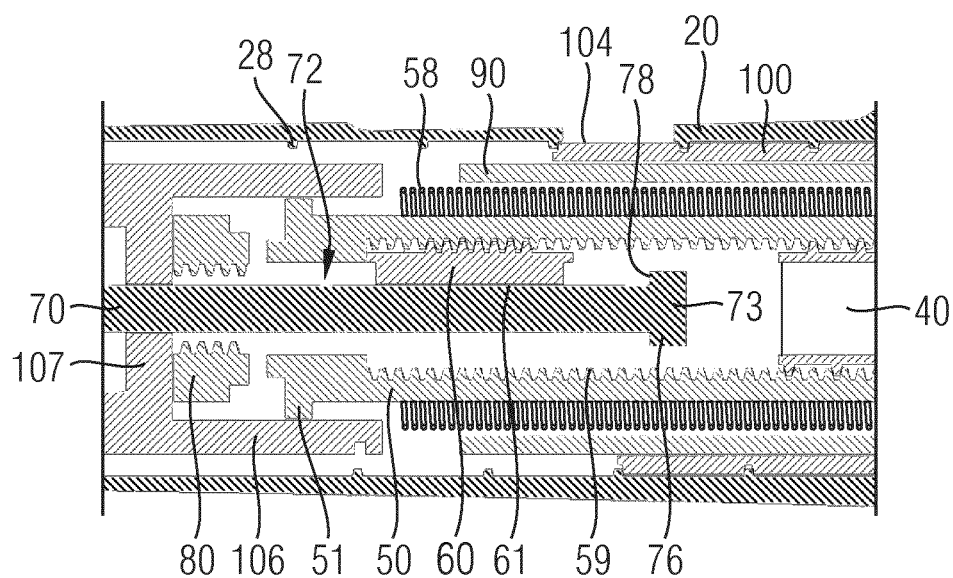
FIG. 16b shows the last dose limiting mechanism in a last dose limiting configuration, FIG. 17a perspectively shows a last dose sleeve in an isolated perspective illustration.

The dose limiting member 60 is not only operable to act as a single dose limiting member but may also provide an alternative or additional last dose limiting mechanism. In FIG. 16*a* a configuration of the drive mechanism 3 is shown, where a proximal end of the piston rod 70 has already left the sleeve of the clutch 40. In this configuration, there might be only 50 I.U. of medicament left in the cartridge 14. For security reasons, the drive mechanism 3 must not set a dose exceeding this residual amount of medicament.

Figure 16B:
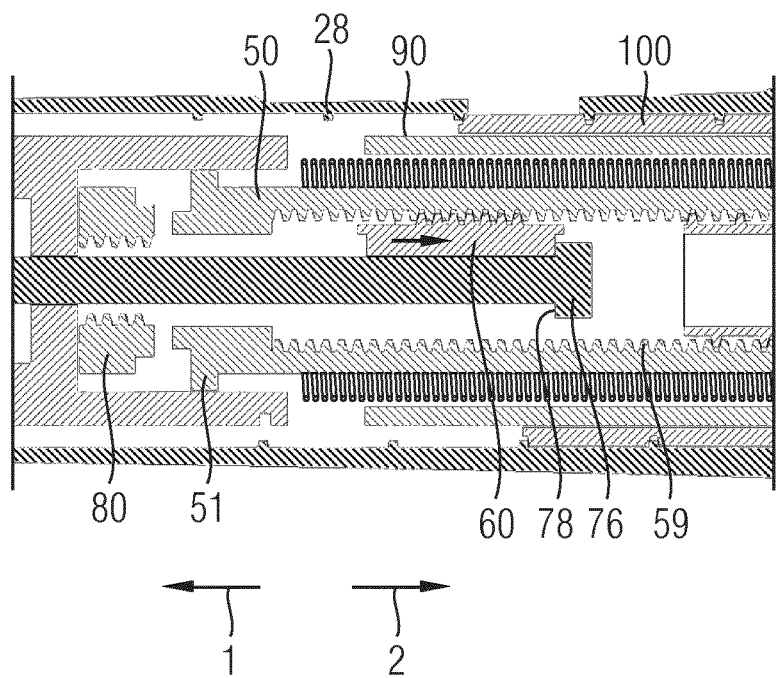

However, dose setting may take place as usual and as described above by rotating the actuation member 30 in a dose incrementing direction. This rotation leads to a corresponding rotation of the drive sleeve 50 and hence to a distally directed displacement of the dose limiting member 60 in proximal direction 2. As shown in FIGS. 16*a* and 16*b*, the dose limiting member 60 slides with a radially inwardly extending gliding portion 61 in a groove 72 of the piston rod 70. Said groove is terminated by a radially extending portion 76 at the proximal end 73 of the piston rod 70.

Hence, the groove 72 is delimited in proximal direction 2 by a last dose stop 78 extending in radial direction. During a dose setting procedure, the drive sleeve 50 is only allowed to rotate relative to piston rod 70 until the axial stop position of the dose limiting member 60 with regard to the piston rod 70 has been reached. Since the dose limiting member 60 as illustrated in FIG. 16*b* is hindered from sliding further in proximal direction 2 along the piston rod 70, a further dose incrementing rotation of the drive sleeve 50 is effectively blocked due to the threaded engagement of the dose limiting member 60 and the drive sleeve 50. Consequently, the dose limiting member effectively provides a last dose limiting mechanism effectively preventing that the drive mechanism 3 is set to a dose exceeding the amount of medicament contained in the cartridge 14.

The last dose limiting functionality of the dose limiting member 60 may be implemented only optionally or alternatively to the last dose limiting mechanism provided by the last dose sleeve 110 as explained above.

| List of Reference Numerals | |
| --- | --- |
| 1 | distal direction |
| 2 | proximal direction |
| 3 | drive mechanism |
| 10 | drug delivery device |
| 12 | cartridge holder |
| 14 | cartridge |
| 16 | piston |
| 17 | protective cap |
| 18 | needle assembly |
| 19 | inner needle cap |
| 20 | housing |
| 21 | spring element |
| 22 | rim |
| 23 | receptacle |
| 24 | socket |
| 25 | window |
| 26 | toothed ring |
| 27 | groove |
| 28 | inner thread |
| 30 | actuation member |
| 32 | flange portion |
| 33 | journal |
| 34 | protrusion |
| 40 | clutch |
| 42 | stop |
| 44 | rib |
| 45 | tooth |
| 46 | snap portion |
| 48 | rim |
| 49 | flange |
| 50 | drive sleeve |
| 51 | ratchet member |
| 52 | groove |
| 53 | tooth |
| 54 | recess |
| 55 | recess |
| 56 | stop |
| 56a | recess |
| 57 | distal face |
| 58 | helical spring |
| 59 | internal thread |
| 60 | dose limiting member |
| 61 | gliding portion |
| 62a | distal stop portion |
| 62b | proximal stop portion |
| 63 | external thread |
| 64 | clicking member |
| 65 | proximal end face |
| 66 | latch portion |
| 67 | distal end face |
| 68 | arm |
| 70 | piston rod |
| 71 | pressure foot |
| 72 | groove |
| 73 | proximal end |
| 74 | thread |
| 76 | radially extending portion |
| 78 | stop |
| 80 | drive nut |
| 82 | proximal face |
| 84 | thread |
| 86 | ratchet member |
| 87 | tooth |
| 90 | intermediate sleeve |
| 92 | protrusion |
| 94 | recess |
| 100 | dose indicating sleeve |
| 102 | protrusion |
| 104 | dose indicating number |
| 105 | toothed surface |
| 106 | insert |
| 107 | protrusion |
| 108 | toothed surface |
| 109 | recess |
| 110 | last dose sleeve |
| 111 | distal flange |
| 112 | distal stop |
| 113 | proximal flange |
| 114 | proximal stop |
| 115 | recess |
| 116 | spring element |
| 117 | rim |
| 118 | toothed surface |
| 119 | thread |
| 120 | last dose member |
| 122 | protrusion |
| 124 | leading edge |
| 126 | trailing edge |
| 128 | internal thread |

The invention claimed is:

1. A drive mechanism for a drug delivery device for dispensing of a dose of a medicament, the drive mechanism comprising:

an elongate housing configured to extend along a longitudinal axis of the drug delivery device, an actuation member rotatably supported on the housing for setting of the dose, a last dose sleeve directly rotatably engaged with the actuation member and having a stop, the last dose sleeve further comprising a radially outwardly extending flange, and a last dose member threadedly engaged with the last dose sleeve, the last dose member further being rotatably fixed to the housing and being operable to engage with the stop to limit rotation of the last dose sleeve relative to the last dose member, wherein the last dose sleeve comprises an external thread mating with an internal thread of the last dose member, the internal thread of the last dose member at least partially surrounding a circumference of the last dose sleeve, and wherein the stop extends radially outwardly at a distal end or a proximal end of the external thread of the last dose sleeve, and wherein the stop protrudes axially from an axial face of the flange, wherein the axial face faces towards and adjoins the external thread.

2. The drive mechanism of claim 1, wherein:

the stop is a first stop, the last dose sleeve comprises a second stop extending radially outwardly at a proximal end of the external thread, and the last dose member is engageable with the first stop in a first circumferential direction and is engageable with the second stop in a second circumferential direction.

3. The drive mechanism according to claim 1, wherein the last dose member comprises a radially outwardly extending protrusion engaged with an axially extending groove of the housing to limit rotation of the last dose member relative to the housing.

4. The drive mechanism according to claim 1, wherein the last dose member is arc-shaped such that the last dose member engages a circumferential portion of the last dose sleeve, the last dose member comprising an edge to engage with the stop of the last dose sleeve in a circumferential direction.

5. The drive mechanism according to claim 1, wherein the last dose sleeve and the last dose member are located in a receptacle at a proximal end of the housing.

6. The drive mechanism according to claim 5, wherein the actuation member is rotatably supported on the proximal end of the housing.

7. The drive mechanism according to claim 5, wherein the actuation member closes the receptacle of the housing.

8. The drive mechanism according to claim 1, wherein the actuation member is displaceable along the longitudinal axis of the drug delivery device in a distal direction relative to the housing against a force of a spring element from a dose setting position to a dose dispensing position.

9. The drive mechanism according to claim 8, wherein, when the actuation member is displaced into the dose dispensing position, the actuation member seals a proximal end of the housing.

10. The drive mechanism according to claim 8, wherein the spring element is helically shaped and is configured to extend in a proximal direction along the longitudinal axis of the drug delivery device from a proximal end of the last dose sleeve, the spring element abuts against an inner proximal end face of the actuation member to bias the actuation member in the proximal direction.

11. The drive mechanism according to claim 1, wherein the last dose sleeve comprises an axial recess to receive a correspondingly shaped distally extending journal of the actuation member such that the last dose sleeve and the actuation member are rotatably coupled.

12. The drive mechanism according to claim 1, wherein the last dose sleeve comprises a radially extending flange portion at a distal end of the last dose sleeve to axially abut with a radially inwardly extending socket portion of the housing such that the last dose sleeve is radially confined in the housing.

13. The drive mechanism according to claim 1, wherein the last dose sleeve is rotatably supported on a clutch at least partially extending into an interior of the last dose sleeve.

14. The drive mechanism according to claim 13, wherein the last dose sleeve comprises a toothed surface at a distal end of a radially inwardly facing side wall of the last dose sleeve to selectively engage with correspondingly shaped radially outwardly extending teeth of the clutch.

15. The drive mechanism according to claim 13, wherein the stop is a dose setting stop, and the clutch comprises a dose limiting stop being operable to engage with a corresponding stop on a dose limiting member to limit a rotation of the clutch relative to the dose limiting member.

16. The drive mechanism according to claim 1, wherein a circumferential edge of the last dose member is operable to engage with the stop of the last dose sleeve.

17. The drive mechanism according to claim 1, wherein the last dose member comprises a leading edge and a trailing edge in a circumferential direction with respect to a sense of rotation of the last dose sleeve relative to the last dose member, and wherein at least one of the leading edge or the trailing edge of the last dose member is configured to abut in the circumferential direction with the stop when the last dose member reaches a last dose limiting configuration.

18. A drug delivery device for dispensing of a dose of a medicament, the drug delivery device comprising:

a drive mechanism comprising an elongate housing extending in an axial direction, an actuation member rotatably supported on the housing for setting of the dose, a last dose sleeve directly rotatably engaged with the actuation member and having a stop, the last dose sleeve further comprising a radially outwardly extending flange, and a last dose member threadedly engaged with the last dose sleeve, further being rotatably fixed to the housing and being operable to engage with the stop to limit a rotation of the last dose sleeve relative to the last dose member, wherein the last dose sleeve comprises an external thread mating with an internal thread of the last dose member, the internal thread of the last dose member at least partially surrounding a circumference of the last dose sleeve, and wherein the stop extends radially outwardly at a distal end or a proximal end of the external thread of the last dose sleeve, and wherein the stop protrudes axially from an axial face of the flange, wherein the axial face faces towards and adjoins the external thread; and a cartridge at least partially filled with the medicament and being engaged to the drive mechanism, the cartridge being arranged in the housing or being arranged in a cartridge holder fixed to the housing.

19. A method of dispensing a dose of a medicament using an injection device comprising an actuation member, the method comprising:

rotating the actuation member to rotate a last dose sleeve of the last dose mechanism relative to a last dose member of the last dose mechanism to set a dose, an external thread of the last dose sleeve mating with an internal thread of the last dose member at least partially surrounding a circumference of the last dose sleeve, the actuation member being directly rotatably engaged with the last dose mechanism such that a stop of the last dose sleeve of the last dose mechanism limits a rotation of the actuation member, the stop extending radially outwardly at a distal end or a proximal end of an external thread of the last dose sleeve, the stop protruding axially from an axial face of a radially outwardly extending flange of the last dose sleeve, and the axial face of the flange facing toward and adjoining the external thread; and depressing the actuation member to dispense the dose.

20. The method of claim 19, wherein rotating the actuation member to rotate the last dose sleeve of the last dose mechanism relative to the last dose member of the last dose mechanism to set the dose comprises rotating the last dose sleeve of the last dose mechanism relative to the last dose member of the last dose mechanism within a dose limit, the stop of the last dose sleeve being operable to engage with the last dose member to limit the rotation of the last dose sleeve relative to the last dose member within the dose limit.

* * * * *